United States Patent
Warnking et al.

(10) Patent No.: US 8,974,445 B2
(45) Date of Patent: Mar. 10, 2015

(54) METHODS AND APPARATUS FOR TREATMENT OF CARDIAC VALVE INSUFFICIENCY

(75) Inventors: Reinhard Warnking, E. Setauket, NY (US); Eugene J. Jung, Nesconset, NY (US); Yong Zou, S. Setauket, NY (US); Jacques Seguin, London (GB); Mano Iyer, Staten Island, NY (US)

(73) Assignee: ReCor Medical, Inc., Palo Alto, CA (US)

(*) Notice: Subject to any disclaimer, the term of this patent is extended or adjusted under 35 U.S.C. 154(b) by 25 days.

(21) Appl. No.: 12/684,067

(22) Filed: Jan. 7, 2010

(65) Prior Publication Data
US 2010/0179424 A1 Jul. 15, 2010

Related U.S. Application Data

(60) Provisional application No. 61/204,744, filed on Jan. 9, 2009.

(51) Int. Cl.
| A61B 18/04 | (2006.01) |
| --- | --- |
| A61N 7/02 | (2006.01) |
| A61B 17/00 | (2006.01) |
| A61B 17/22 | (2006.01) |
| A61B 18/00 | (2006.01) |
| A61B 19/00 | (2006.01) |
| A61N 7/00 | (2006.01) |

(52) U.S. Cl.
CPC ....... *A61N 7/022* (2013.01); *A61B 2017/00106* (2013.01); *A61B 2017/00703* (2013.01); *A61B 2017/22051* (2013.01); *A61B 2018/00023* (2013.01); *A61B 2019/5276* (2013.01); *A61N 2007/0078* (2013.01)

USPC .................................................. 606/27; 601/3

(58) Field of Classification Search
USPC ............ 606/27–46; 601/2–3; 607/96; 604/22
See application file for complete search history.

(56) References Cited

U.S. PATENT DOCUMENTS

| 3,168,659 A | 2/1965 | Bayre et al. |
| --- | --- | --- |
| 4,055,190 A | 10/1977 | Tany et al. |
| 4,084,582 A | 4/1978 | Nigam |
| 4,185,501 A | 1/1980 | Proudian et al. |
| 4,194,510 A | 3/1980 | Proudian |
| 4,338,942 A | 7/1982 | Fogarty |
| 4,381,007 A | 4/1983 | Doss |

(Continued)

FOREIGN PATENT DOCUMENTS

| EP | 0659387 | 6/1995 |
| --- | --- | --- |
| EP | 0 774 276 | 5/1997 |

(Continued)

OTHER PUBLICATIONS

International Search Report for PCT/US2010/020333, mailed Feb. 25, 2010, 3 pages.

(Continued)

*Primary Examiner* — Ruth S Smith

(57) ABSTRACT

Mitral valve insufficiency is treated by introducing an expansible device such as a balloon bearing an ultrasonic transducer into the heart so that the transducer is positioned adjacent the mitral annulus but spaced from the mitral annulus, and actuating the transducer to heat the mitral annulus, denature collagen in the annulus and thereby shrink the annulus.

5 Claims, 6 Drawing Sheets

(56) References Cited

U.S. PATENT DOCUMENTS

| | | |
|---|---|---|
| 4,387,720 A | 6/1983 | Miller |
| 4,391,281 A | 7/1983 | Green |
| 4,402,307 A | 9/1983 | Hanson et al. |
| 4,403,612 A | 9/1983 | Fogarty |
| 4,422,447 A | 12/1983 | Schiff |
| 4,433,692 A | 2/1984 | Baba |
| 4,602,624 A | 7/1986 | Naples et al. |
| 4,643,186 A | 2/1987 | Rosen et al. |
| 4,650,466 A | 3/1987 | Luther |
| 4,672,961 A | 6/1987 | Davies |
| 4,680,499 A | 7/1987 | Umemura et al. |
| 4,685,334 A | 8/1987 | Latimer |
| 4,691,714 A | 9/1987 | Wong et al. |
| 4,722,347 A | 2/1988 | Abrams et al. |
| 4,744,366 A | 5/1988 | Jang |
| 4,785,815 A | 11/1988 | Cohen |
| 4,800,316 A | 1/1989 | Ju-Zhen |
| 4,813,934 A | 3/1989 | Engelson et al. |
| 4,841,977 A | 6/1989 | Griffith et al. |
| 4,869,263 A | 9/1989 | Segal et al. |
| 4,914,510 A | 4/1990 | Brenneshoz et al. |
| 4,945,912 A | 8/1990 | Langberg |
| 4,972,826 A | 11/1990 | Koehler et al. |
| 4,976,711 A | 12/1990 | Parins et al. |
| 4,983,169 A | 1/1991 | Furukawa |
| 5,006,119 A | 4/1991 | Acker et al. |
| 5,019,034 A | 5/1991 | Weaver et al. |
| 5,104,393 A | 4/1992 | Isner |
| 5,105,116 A | 4/1992 | Okamoto et al. |
| 5,114,423 A | 5/1992 | Kasprzyk et al. |
| 5,117,831 A | 6/1992 | Jang et al. |
| 5,125,928 A | 6/1992 | Parins et al. |
| 5,135,001 A | 8/1992 | Sinofsky et al. |
| 5,140,987 A | 8/1992 | Schuger |
| 5,160,336 A | 11/1992 | Favre |
| 5,167,233 A | 12/1992 | Eberle et al. |
| 5,175,711 A | 12/1992 | Fujita et al. |
| 5,203,326 A | 4/1993 | Collins |
| 5,209,299 A | 5/1993 | Ayres |
| 5,213,098 A | 5/1993 | Bennett et al. |
| 5,217,454 A | 6/1993 | Khoury |
| 5,226,421 A | 7/1993 | Frisbie et al. |
| 5,226,430 A | 7/1993 | Spears et al. |
| 5,240,005 A | 8/1993 | Viebach |
| 5,242,438 A | 9/1993 | Saadatmanesh et al. |
| 5,242,441 A | 9/1993 | Avitall |
| 5,246,438 A | 9/1993 | Langberg |
| 5,269,291 A | 12/1993 | Carter |
| 5,281,213 A | 1/1994 | Milder et al. |
| 5,281,218 A | 1/1994 | Imran |
| 5,282,785 A | 2/1994 | Shapland et al. |
| 5,286,254 A | 2/1994 | Shapland et al. |
| 5,293,868 A | 3/1994 | Nardella |
| 5,295,484 A | 3/1994 | Marcus et al. |
| 5,300,068 A | 4/1994 | Rosar et al. |
| 5,304,120 A | 4/1994 | Crandell et al. |
| 5,305,731 A | 4/1994 | Buchholtz |
| 5,305,755 A | 4/1994 | Nakao |
| 5,324,255 A | 6/1994 | Passafaro et al. |
| 5,324,259 A | 6/1994 | Taylor et al. |
| 5,327,885 A | 7/1994 | Griffith |
| 5,334,193 A | 8/1994 | Nardella |
| 5,338,295 A | 8/1994 | Cornelius et al. |
| 5,342,292 A | 8/1994 | Nita et al. |
| 5,348,010 A | 9/1994 | Schnall et al. |
| 5,364,388 A | 11/1994 | Koziol |
| 5,368,591 A | 11/1994 | Lennox et al. |
| 5,385,148 A | 1/1995 | Lesh et al. |
| 5,391,197 A | 2/1995 | Burdette et al. |
| 5,415,654 A | 5/1995 | Daikuzono |
| 5,419,335 A | 5/1995 | Hartmann et al. |
| 5,421,338 A | 6/1995 | Crowley et al. |
| 5,423,319 A | 6/1995 | Seyed-Bolorforosh |
| 5,423,744 A | 6/1995 | Gencheff et al. |
| 5,423,755 A | 6/1995 | Kesten |
| 5,423,807 A | 6/1995 | Milder |
| 5,431,663 A | 7/1995 | Carter |
| 5,452,733 A | 9/1995 | Sterman et al. |
| 5,454,782 A | 10/1995 | Perkins |
| 5,458,568 A | 10/1995 | Racchini et al. |
| 5,458,626 A | 10/1995 | Krause |
| 5,468,239 A | 11/1995 | Tanner |
| 5,470,352 A | 11/1995 | Rappaport |
| 5,471,988 A | 12/1995 | Fujio et al. |
| 5,472,406 A | 12/1995 | de la Torre et al. |
| 5,477,736 A | 12/1995 | Lorraine |
| 5,484,400 A | 1/1996 | Edwards et al. |
| 5,488,955 A | 2/1996 | Dias |
| 5,492,532 A | 2/1996 | Ryan et al. |
| 5,498,238 A | 3/1996 | Shapland et al. |
| 5,499,971 A | 3/1996 | Shapland et al. |
| 5,505,700 A | 4/1996 | Leone et al. |
| 5,507,724 A | 4/1996 | Hofmann et al. |
| 5,513,639 A | 5/1996 | Satomi et al. |
| 5,549,644 A | 8/1996 | Lundquist et al. |
| 5,553,611 A | 9/1996 | Budd et al. |
| 5,562,720 A | 10/1996 | Stern et al. |
| 5,569,198 A | 10/1996 | Racchini et al. |
| 5,571,088 A | 11/1996 | Lennox et al. |
| 5,571,147 A | 11/1996 | Sluijter et al. |
| 5,571,215 A | 11/1996 | Sterman et al. |
| 5,571,216 A | 11/1996 | Anderson |
| 5,575,766 A | 11/1996 | Swartz et al. |
| 5,575,787 A | 11/1996 | Abela et al. |
| 5,582,609 A | 12/1996 | Swanson et al. |
| 5,596,989 A | 1/1997 | Morita |
| 5,599,345 A | 2/1997 | Edwards et al. |
| 5,606,974 A | 3/1997 | Castellano et al. |
| 5,620,479 A | 4/1997 | Diederich |
| 5,626,576 A | 5/1997 | Janssen |
| 5,628,730 A | 5/1997 | Shapland et al. |
| 5,630,837 A | 5/1997 | Crowley |
| 5,634,899 A | 6/1997 | Shapland et al. |
| 5,643,279 A | 7/1997 | Trotta |
| 5,655,539 A | 8/1997 | Wang |
| 5,669,932 A | 9/1997 | Fischell et al. |
| 5,672,174 A | 9/1997 | Gough et al. |
| D384,743 S | 10/1997 | Chia |
| 5,676,692 A | 10/1997 | Sanghui |
| 5,688,266 A | 11/1997 | Edwards et al. |
| 5,690,691 A | 11/1997 | Chen et al. |
| 5,693,043 A | 12/1997 | Kittrell |
| 5,704,361 A | 1/1998 | Seward et al. |
| 5,707,352 A | 1/1998 | Sekins et al. |
| 5,713,849 A | 2/1998 | Bosma et al. |
| 5,720,287 A | 2/1998 | Chapelon et al. |
| 5,722,397 A | 3/1998 | Eppstein |
| 5,722,401 A | 3/1998 | Pietroski et al. |
| 5,762,066 A | 6/1998 | Law et al. |
| 5,767,692 A | 6/1998 | Antonello et al. |
| 5,769,812 A | 6/1998 | Stevens et al. |
| 5,772,590 A | 6/1998 | Webster, Jr. |
| 5,776,141 A | 7/1998 | Klein et al. |
| 5,779,715 A | 7/1998 | Tu |
| 5,782,760 A | 7/1998 | Schaer |
| 5,782,828 A | 7/1998 | Chen et al. |
| 5,782,900 A | 7/1998 | de la Rama et al. |
| 5,792,140 A | 8/1998 | Tu et al. |
| 5,792,187 A | 8/1998 | Adams |
| 5,800,392 A | 9/1998 | Racchini |
| 5,807,306 A | 9/1998 | Shapland et al. |
| 5,810,802 A | 9/1998 | Panescu et al. |
| 5,817,018 A | 10/1998 | Ohtomo |
| 5,824,087 A | 10/1998 | Aspden et al. |
| 5,840,031 A | 11/1998 | Crowley |
| 5,840,066 A | 11/1998 | Matsuda |
| 5,840,076 A | 11/1998 | Swanson et al. |
| 5,843,020 A | 12/1998 | Tu et al. |
| 5,843,152 A | 12/1998 | Tu et al. |
| 5,848,969 A | 12/1998 | Panescu et al. |
| 5,849,028 A | 12/1998 | Chen et al. |
| 5,853,368 A | 12/1998 | Solomon et al. |
| 5,860,974 A | 1/1999 | Abele |
| 5,861,021 A | 1/1999 | Thome et al. |

(56) References Cited

U.S. PATENT DOCUMENTS

| | | |
|---|---|---|
| 5,863,291 A | 1/1999 | Schaer |
| 5,865,787 A | 2/1999 | Shapland et al. |
| 5,865,801 A | 2/1999 | Houser |
| 5,868,708 A | 2/1999 | Hart et al. |
| 5,868,741 A | 2/1999 | Chia et al. |
| 5,868,779 A | 2/1999 | Ruiz |
| 5,871,449 A | 2/1999 | Brown |
| 5,876,399 A | 3/1999 | Chia et al. |
| 5,882,333 A | 3/1999 | Schaer et al. |
| 5,891,027 A | 4/1999 | Tu et al. |
| 5,891,135 A | 4/1999 | Jackson |
| 5,891,137 A | 4/1999 | Chia et al. |
| 5,891,138 A | 4/1999 | Tu et al. |
| 5,893,885 A | 4/1999 | Webster, Jr. |
| 5,895,355 A | 4/1999 | Schaer |
| 5,897,554 A | 4/1999 | Chia et al. |
| 5,906,636 A | 5/1999 | Casscells, III et al. |
| 5,916,170 A | 6/1999 | Kolz et al. |
| 5,916,213 A | 6/1999 | Haissaguerre et al. |
| 5,919,187 A | 7/1999 | Guglielmi et al. |
| 5,921,982 A | 7/1999 | Lesh et al. |
| 5,924,997 A | 7/1999 | Campbell |
| 5,931,811 A | 8/1999 | Haissaguerre |
| 5,935,063 A | 8/1999 | Nguyen |
| 5,935,075 A | 8/1999 | Casscells et al. |
| 5,938,660 A | 8/1999 | Swartz et al. |
| 5,941,845 A | 8/1999 | Tu et al. |
| 5,944,710 A | 8/1999 | Dev et al. |
| 5,954,649 A | 9/1999 | Chia et al. |
| 5,954,719 A | 9/1999 | Chen et al. |
| 5,954,751 A | 9/1999 | Chen et al. |
| 5,964,751 A | 10/1999 | Amplatz |
| 5,971,968 A | 10/1999 | Tu et al. |
| 5,971,983 A | 10/1999 | Lesh |
| 5,972,026 A | 10/1999 | Laufer et al. |
| 5,980,515 A | 11/1999 | Tu |
| 6,002,955 A | 12/1999 | Willems |
| 6,002,956 A | 12/1999 | Schaer |
| 6,004,269 A | 12/1999 | Crowley et al. |
| 6,006,123 A | 12/1999 | Nguyen et al. |
| 6,009,877 A | 1/2000 | Edwards |
| 6,011,995 A | 1/2000 | Guglielmi et al. |
| 6,012,457 A | 1/2000 | Lesh |
| 6,013,053 A | 1/2000 | Bower et al. |
| 6,016,437 A | 1/2000 | Tu et al. |
| 6,017,274 A | 1/2000 | Sherman et al. |
| 6,022,319 A | 2/2000 | Willard |
| 6,024,740 A | 2/2000 | Lesh et al. |
| 6,026,326 A | 2/2000 | Bardy |
| 6,033,402 A | 3/2000 | Tu et al. |
| 6,033,403 A | 3/2000 | Tu et al. |
| 6,041,252 A | 3/2000 | Walker et al. |
| 6,055,859 A | 5/2000 | Kozuka et al. |
| 6,056,744 A | 5/2000 | Edwards |
| 6,058,328 A | 5/2000 | Levine et al. |
| 6,059,423 A | 5/2000 | Knopick |
| 6,063,077 A | 5/2000 | Schaer |
| 6,064,902 A | 5/2000 | Haissaguerre |
| 6,066,134 A | 5/2000 | Eggers et al. |
| 6,068,629 A | 5/2000 | Haissaguerre et al. |
| 6,071,279 A | 6/2000 | Whayne |
| 6,073,052 A | 6/2000 | Zelickson et al. |
| 6,080,151 A | 6/2000 | Swartz et al. |
| 6,083,255 A | 7/2000 | Laufer et al. |
| 6,094,988 A | 8/2000 | Aindow |
| 6,096,054 A | 8/2000 | Wyzgala et al. |
| 6,102,908 A | 8/2000 | Tu et al. |
| 6,106,474 A | 8/2000 | Koger et al. |
| 6,112,123 A | 8/2000 | Kelleher et al. |
| 6,117,101 A | 9/2000 | Diederich et al. |
| 6,123,456 A | 9/2000 | Lyons |
| 6,128,522 A | 10/2000 | Acker et al. |
| 6,135,999 A | 10/2000 | Fanton et al. |
| 6,146,379 A | 11/2000 | Fleischman |
| 6,149,620 A | 11/2000 | Baker et al. |
| 6,152,144 A | 11/2000 | Lesh et al. |
| 6,152,920 A | 11/2000 | Thompson |
| 6,161,543 A | 12/2000 | Cox et al. |
| 6,163,716 A | 12/2000 | Edwards |
| 6,164,283 A | 12/2000 | Lesh |
| 6,166,092 A | 12/2000 | Sekins et al. |
| 6,171,306 B1 | 1/2001 | Swanson et al. |
| 6,183,492 B1 | 2/2001 | Hart et al. |
| 6,190,353 B1 | 2/2001 | Makower et al. |
| 6,190,382 B1 | 2/2001 | Ormsby |
| 6,193,713 B1 | 2/2001 | Geistert et al. |
| 6,196,059 B1 | 3/2001 | Kosslinger et al. |
| 6,197,023 B1 | 3/2001 | Muntermann |
| 6,200,269 B1 | 3/2001 | Lin et al. |
| 6,200,315 B1 | 3/2001 | Gaiser et al. |
| 6,200,333 B1 | 3/2001 | Laufer |
| 6,203,525 B1 | 3/2001 | Whayne |
| 6,203,531 B1 | 3/2001 | Ockuly et al. |
| 6,206,831 B1 | 3/2001 | Suorsa |
| 6,208,142 B1 | 3/2001 | Wagshul |
| 6,210,356 B1 | 4/2001 | Anderson et al. |
| 6,212,426 B1 | 4/2001 | Swanson |
| 6,217,576 B1 | 4/2001 | Tu et al. |
| 6,221,070 B1 | 4/2001 | Tu et al. |
| 6,224,592 B1 | 5/2001 | Eggers et al. |
| 6,231,561 B1 | 5/2001 | Frazier |
| 6,233,477 B1 | 5/2001 | Chia et al. |
| 6,235,025 B1 | 5/2001 | Swartz et al. |
| 6,237,605 B1 | 5/2001 | Vaska et al. |
| 6,238,335 B1 | 5/2001 | Silverman et al. |
| 6,238,390 B1 | 5/2001 | Tu et al. |
| 6,240,307 B1 | 5/2001 | Beatty et al. |
| 6,241,692 B1 | 6/2001 | Tu et al. |
| 6,241,726 B1 | 6/2001 | Chia et al. |
| 6,241,727 B1 | 6/2001 | Tu et al. |
| 6,241,754 B1 | 6/2001 | Swanson et al. |
| 6,245,026 B1 | 6/2001 | Campbell et al. |
| 6,245,064 B1 | 6/2001 | Lesh et al. |
| 6,245,067 B1 | 6/2001 | Tu et al. |
| 6,246,899 B1 | 6/2001 | Chia et al. |
| 6,246,912 B1 | 6/2001 | Sluijter |
| 6,246,914 B1 | 6/2001 | de la Rama et al. |
| 6,251,107 B1 | 6/2001 | Schaer |
| 6,251,109 B1 | 6/2001 | Hassett et al. |
| 6,251,130 B1 | 6/2001 | Dobak, III et al. |
| 6,254,598 B1 | 7/2001 | Edwards et al. |
| 6,254,599 B1 | 7/2001 | Lesh et al. |
| 6,259,941 B1 | 7/2001 | Chia et al. |
| 6,272,377 B1 | 8/2001 | Sweeney et al. |
| 6,273,886 B1 | 8/2001 | Edwards et al. |
| 6,273,907 B1 | 8/2001 | Laufer |
| 6,278,351 B1 | 8/2001 | Wheatley |
| 6,280,402 B1 | 8/2001 | Ishibashi et al. |
| 6,282,949 B1 | 9/2001 | Axelsson |
| 6,283,127 B1 | 9/2001 | Sterman et al. |
| 6,283,988 B1 | 9/2001 | Laufer et al. |
| 6,283,989 B1 | 9/2001 | Laufer et al. |
| 6,287,306 B1 | 9/2001 | Kroll et al. |
| 6,290,674 B1 | 9/2001 | Roue et al. |
| 6,290,697 B1 | 9/2001 | Tu et al. |
| 6,292,695 B1 | 9/2001 | Webster, Jr. et al. |
| 6,299,633 B1 | 10/2001 | Laufer |
| 6,302,875 B1 | 10/2001 | Makower et al. |
| 6,302,880 B1 | 10/2001 | Schaer |
| 6,305,378 B1 | 10/2001 | Lesh |
| 6,306,133 B1 | 10/2001 | Tu et al. |
| 6,308,090 B1 | 10/2001 | Tu et al. |
| 6,311,692 B1 | 11/2001 | Vaska et al. |
| 6,314,325 B1 | 11/2001 | Fitz |
| 6,314,962 B1 | 11/2001 | Vaska et al. |
| 6,314,963 B1 | 11/2001 | Vaska et al. |
| 6,315,778 B1 | 11/2001 | Gambale et al. |
| 6,321,121 B1 | 11/2001 | Zelickson et al. |
| 6,322,558 B1 | 11/2001 | Taylor et al. |
| 6,322,559 B1 | 11/2001 | Daulton et al. |
| 6,328,699 B1 | 12/2001 | Eigler et al. |
| 6,330,473 B1 | 12/2001 | Swanson et al. |
| 6,332,880 B1 | 12/2001 | Yang et al. |
| 6,347,247 B1 | 2/2002 | Dev et al. |

(56) References Cited

U.S. PATENT DOCUMENTS

| | | |
|---|---|---|
| 6,355,030 B1 | 3/2002 | Aldrich et al. |
| 6,355,051 B1 | 3/2002 | Sisskind et al. |
| 6,383,151 B1 | 5/2002 | Diederich et al. |
| 6,398,792 B1 | 6/2002 | O'Connor |
| 6,400,982 B2 | 6/2002 | Sweeney et al. |
| 6,405,732 B1 | 6/2002 | Edwards et al. |
| 6,411,852 B1 | 6/2002 | Danek et al. |
| 6,413,255 B1 | 7/2002 | Stern |
| 6,423,026 B1 | 7/2002 | Gesswein et al. |
| 6,447,443 B1 | 9/2002 | Keogh et al. |
| 6,461,314 B1 | 10/2002 | Pant et al. |
| 6,466,811 B1 | 10/2002 | Hassett |
| 6,485,489 B2 | 11/2002 | Teirstein et al. |
| 6,488,673 B1 | 12/2002 | Laufer et al. |
| 6,488,679 B1 | 12/2002 | Swanson et al. |
| 6,491,710 B2 | 12/2002 | Stake |
| 6,492,762 B1 | 12/2002 | Pant et al. |
| 6,500,174 B1 | 12/2002 | Maguire et al. |
| 6,501,978 B2 | 12/2002 | Wagshul et al. |
| 6,506,189 B1 | 1/2003 | Rittman, III et al. |
| 6,508,774 B1 | 1/2003 | Acker et al. |
| 6,513,385 B1 | 2/2003 | Han et al. |
| 6,514,246 B1 | 2/2003 | Swanson et al. |
| 6,514,249 B1 | 2/2003 | Maguire et al. |
| 6,517,536 B2 | 2/2003 | Hooven et al. |
| 6,517,811 B2 | 2/2003 | John et al. |
| 6,522,930 B1 | 2/2003 | Schaer et al. |
| 6,527,769 B2 | 3/2003 | Langberg et al. |
| 6,536,949 B1 | 3/2003 | Heuser |
| 6,540,744 B2 | 4/2003 | Hassett et al. |
| 6,542,251 B2 | 4/2003 | Mueller-Rentz |
| 6,543,274 B1 | 4/2003 | Herrmann et al. |
| 6,547,788 B1 | 4/2003 | Maguire et al. |
| 6,564,096 B2 | 5/2003 | Mest |
| 6,589,274 B2 | 7/2003 | Stiger et al. |
| 6,595,989 B1 | 7/2003 | Schaer |
| 6,599,256 B1 | 7/2003 | Acker et al. |
| 6,599,288 B2 | 7/2003 | Maguire et al. |
| 6,601,459 B1 | 8/2003 | Jenni |
| 6,605,084 B2 | 8/2003 | Acker et al. |
| 6,607,476 B1 | 8/2003 | Barnhart |
| 6,607,502 B1 | 8/2003 | Maguire et al. |
| 6,611,720 B2 | 8/2003 | Hata et al. |
| 6,613,045 B1 | 9/2003 | Laufer et al. |
| 6,615,071 B1 | 9/2003 | Casscells, III et al. |
| 6,622,041 B2 | 9/2003 | Terry, Jr. et al. |
| 6,622,731 B2 | 9/2003 | Daniel et al. |
| 6,626,855 B1 | 9/2003 | Weng et al. |
| 6,626,861 B1 | 9/2003 | Hart et al. |
| 6,626,899 B2 | 9/2003 | Houser et al. |
| 6,634,363 B1 | 10/2003 | Laufer et al. |
| 6,635,054 B2 | 10/2003 | Fjield et al. |
| 6,641,579 B1 | 11/2003 | Bernardi et al. |
| 6,642,515 B1 | 11/2003 | Yamaguchi |
| 6,645,199 B1 | 11/2003 | Jenkens et al. |
| 6,645,202 B1 | 11/2003 | Pless et al. |
| 6,652,515 B1 | 11/2003 | Maguire et al. |
| 6,652,547 B2 | 11/2003 | Rabiner et al. |
| 6,654,636 B1 | 11/2003 | Dev et al. |
| 6,656,136 B1 | 12/2003 | Weng et al. |
| 6,656,174 B1 | 12/2003 | Hegde et al. |
| 6,658,279 B2 | 12/2003 | Swanson et al. |
| 6,660,013 B2 | 12/2003 | Rabiner et al. |
| 6,669,655 B1 | 12/2003 | Acker et al. |
| 6,669,687 B1 | 12/2003 | Saadat |
| 6,671,533 B2 | 12/2003 | Chen et al. |
| 6,671,556 B2 | 12/2003 | Osorio et al. |
| 6,672,312 B2 | 1/2004 | Acker |
| 6,695,782 B2 | 2/2004 | Ranucci et al. |
| 6,718,208 B2 | 4/2004 | Hill et al. |
| 6,719,694 B2 | 4/2004 | Weng et al. |
| 6,719,755 B2 | 4/2004 | Sliwa, Jr. et al. |
| 6,728,563 B2 | 4/2004 | Rashidi |
| 6,733,451 B2 | 5/2004 | Rabiner et al. |
| 6,735,471 B2 | 5/2004 | Hill et al. |
| 6,740,082 B2 | 5/2004 | Shadduck |
| 6,740,107 B2 | 5/2004 | Loeb et al. |
| 6,743,239 B1 | 6/2004 | Kuehn et al. |
| 6,752,805 B2 | 6/2004 | Maguire et al. |
| 6,758,830 B1 | 7/2004 | Schaer et al. |
| 6,763,722 B2 | 7/2004 | Fjield et al. |
| 6,764,486 B2 | 7/2004 | Natale |
| 6,786,904 B2 | 9/2004 | Doscher et al. |
| 6,787,974 B2 | 9/2004 | Fjield et al. |
| 6,799,064 B1 | 9/2004 | Hassett et al. |
| 6,805,128 B1 | 10/2004 | Pless et al. |
| 6,808,524 B2 | 10/2004 | Lopath et al. |
| 6,837,886 B2 | 1/2005 | Collins et al. |
| 6,840,936 B2 | 1/2005 | Sliwa et al. |
| 6,845,267 B2 | 1/2005 | Harrison et al. |
| 6,850,801 B2 | 2/2005 | Kieval et al. |
| 6,862,479 B1 | 3/2005 | Whitehurst et al. |
| 6,866,760 B2 | 3/2005 | Paolini, Jr. et al. |
| 6,869,431 B2 | 3/2005 | Maguire et al. |
| 6,885,888 B2 | 4/2005 | Rezai |
| 6,929,608 B1 | 8/2005 | Hutchinson et al. |
| 6,936,046 B2 | 8/2005 | Hissong et al. |
| 6,936,047 B2 | 8/2005 | Nasab et al. |
| 6,939,309 B1 | 9/2005 | Beatty et al. |
| 6,939,346 B2 | 9/2005 | Kannenberg et al. |
| 6,947,785 B1 | 9/2005 | Beatty et al. |
| 6,960,207 B2 | 11/2005 | Vanney et al. |
| 6,964,660 B2 | 11/2005 | Maguire et al. |
| 6,966,908 B2 | 11/2005 | Maguire et al. |
| 6,969,388 B2 | 11/2005 | Goldman et al. |
| 6,976,492 B2 | 12/2005 | Ingle et al. |
| 6,978,174 B2 | 12/2005 | Gelfand et al. |
| 6,984,232 B2 | 1/2006 | Vanney et al. |
| 6,990,370 B1 | 1/2006 | Beatty et al. |
| 6,997,925 B2 | 2/2006 | Maguire et al. |
| 7,004,911 B1 | 2/2006 | Tu et al. |
| 7,027,869 B2 | 4/2006 | Danek et al. |
| 7,052,493 B2 | 5/2006 | Vaska et al. |
| 7,054,685 B2 | 5/2006 | Dimmer et al. |
| 7,063,679 B2 | 6/2006 | Maguire et al. |
| 7,081,114 B2 | 7/2006 | Rashidi |
| 7,081,115 B2 | 7/2006 | Taimisto |
| 7,082,336 B2 | 7/2006 | Ransbury et al. |
| 7,083,614 B2 | 8/2006 | Fjield et al. |
| 7,089,063 B2 | 8/2006 | Lesh et al. |
| 7,104,987 B2 | 9/2006 | Biggs et al. |
| 7,122,019 B1 | 10/2006 | Kesten et al. |
| 7,137,963 B2 | 11/2006 | Nita et al. |
| 7,155,284 B1 | 12/2006 | Whitehurst et al. |
| 7,156,816 B2 | 1/2007 | Schwartz et al. |
| 7,158,832 B2 | 1/2007 | Kieval et al. |
| 7,162,303 B2 | 1/2007 | Levin et al. |
| 7,189,203 B2 | 3/2007 | Lau et al. |
| 7,189,229 B2 | 3/2007 | Lopath et al. |
| 7,191,015 B2 | 3/2007 | Lamson et al. |
| 7,195,628 B2 | 3/2007 | Falkenberg |
| 7,198,635 B2 | 4/2007 | Danek et al. |
| 7,211,045 B2 | 5/2007 | Dala-Krishna et al. |
| 7,211,055 B2 | 5/2007 | Diederich |
| 7,217,284 B2 | 5/2007 | Houser et al. |
| 7,229,437 B2 | 6/2007 | Johnson et al. |
| 7,229,469 B1 | 6/2007 | Witzel et al. |
| 7,263,397 B2 | 8/2007 | Hauck et al. |
| 7,269,453 B2 | 9/2007 | Mogul |
| 7,285,116 B2 | 10/2007 | de la Rama et al. |
| 7,311,701 B2 | 12/2007 | Gifford et al. |
| 7,326,201 B2 | 2/2008 | Fjield et al. |
| 7,338,434 B1 | 3/2008 | Haarstad et al. |
| 7,340,307 B2 | 3/2008 | Maguire |
| 7,373,204 B2 | 5/2008 | Gelfand et al. |
| 7,387,126 B2 | 6/2008 | Cox et al. |
| 7,387,629 B2 | 6/2008 | Vanney et al. |
| 7,425,212 B1 | 9/2008 | Danek et al. |
| 7,444,183 B2 | 10/2008 | Knudson et al. |
| 7,503,895 B2 | 3/2009 | Rabiner et al. |
| 7,507,235 B2 | 3/2009 | Keogh et al. |
| 7,529,582 B1 | 5/2009 | DiLorenzo |
| 7,529,589 B2 | 5/2009 | Williams et al. |
| 7,532,938 B2 | 5/2009 | Machado et al. |

(56) References Cited

U.S. PATENT DOCUMENTS

| | | |
|---|---|---|
| 7,540,846 B2 | 6/2009 | Harhen et al. |
| 7,591,996 B2 | 9/2009 | Hwang et al. |
| 7,599,736 B2 | 10/2009 | DiLorenzo |
| 7,616,997 B2 | 11/2009 | Kieval et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,647,115 B2 | 1/2010 | Levin et al. |
| 7,653,438 B2 | 1/2010 | Deem et al. |
| 7,670,297 B1 | 3/2010 | Hauck et al. |
| 7,678,104 B2 | 3/2010 | Keidar |
| 7,706,882 B2 | 4/2010 | Francischelli et al. |
| RE41,334 E | 5/2010 | Beatty et al. |
| 7,717,948 B2 | 5/2010 | Demarais et al. |
| 7,725,196 B2 | 5/2010 | Machado et al. |
| 7,756,583 B2 | 7/2010 | Demarais et al. |
| 7,756,683 B2 | 7/2010 | Kilgus |
| 7,819,826 B2 | 10/2010 | Diederich et al. |
| 7,819,866 B2 | 10/2010 | Bednarek |
| 7,824,341 B2 | 11/2010 | Krishnan |
| 7,837,676 B2 | 11/2010 | Sinelnikov et al. |
| 7,864,275 B2 | 1/2011 | Teramoto et al. |
| 7,873,417 B2 | 1/2011 | Demarais et al. |
| 7,881,809 B2 | 2/2011 | Rashidi |
| 7,925,352 B2 | 4/2011 | Stack et al. |
| 7,937,143 B2 | 5/2011 | Demarais et al. |
| 7,955,293 B2 | 6/2011 | Nita et al. |
| 8,040,612 B2 | 10/2011 | Suijver et al. |
| 8,088,127 B2 | 1/2012 | Mayse et al. |
| 8,116,883 B2 | 2/2012 | Williams et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,155,744 B2 | 4/2012 | Rezai |
| 8,175,711 B2 | 5/2012 | Demarais et al. |
| 8,347,891 B2 | 1/2013 | Demarais et al. |
| 2001/0007070 A1 | 7/2001 | Stewart et al. |
| 2001/0007940 A1 | 7/2001 | Tu et al. |
| 2001/0044625 A1 | 11/2001 | Hata et al. |
| 2002/0002329 A1 | 1/2002 | Avitall |
| 2002/0019627 A1 | 2/2002 | Maguire et al. |
| 2002/0022833 A1 | 2/2002 | Maguire et al. |
| 2002/0062123 A1 | 5/2002 | McClurken et al. |
| 2002/0065512 A1 | 5/2002 | Fjield et al. |
| 2002/0065541 A1 | 5/2002 | Fredricks et al. |
| 2002/0068885 A1 | 6/2002 | Harhen et al. |
| 2002/0082594 A1 | 6/2002 | Hata et al. |
| 2002/0087156 A1 | 7/2002 | Maguire |
| 2002/0165532 A1 | 11/2002 | Hill et al. |
| 2002/0165535 A1 | 11/2002 | Lesh et al. |
| 2002/0183682 A1 | 12/2002 | Darvish et al. |
| 2003/0013968 A1 | 1/2003 | Fjield et al. |
| 2003/0018367 A1 | 1/2003 | DiLorenzo |
| 2003/0036705 A1 | 2/2003 | Hare et al. |
| 2003/0050632 A1 | 3/2003 | Fjield et al. |
| 2003/0050637 A1 | 3/2003 | Maguire et al. |
| 2003/0050681 A1 | 3/2003 | Pianca et al. |
| 2003/0055422 A1 | 3/2003 | Lesh |
| 2003/0065263 A1 | 4/2003 | Hare et al. |
| 2003/0069570 A1 | 4/2003 | Witzel et al. |
| 2003/0109778 A1 | 6/2003 | Rashidi |
| 2003/0114901 A1 | 6/2003 | Loeb et al. |
| 2003/0125790 A1 | 7/2003 | Fastovsky et al. |
| 2003/0138571 A1 | 7/2003 | Kunishi et al. |
| 2003/0150464 A1 | 8/2003 | Casscells |
| 2003/0158584 A1 | 8/2003 | Cates et al. |
| 2003/0181897 A1 | 9/2003 | Thomas et al. |
| 2003/0199747 A1 | 10/2003 | Michlitsch et al. |
| 2003/0199767 A1 | 10/2003 | Cespedes et al. |
| 2003/0199768 A1 | 10/2003 | Cespedes et al. |
| 2003/0199863 A1 | 10/2003 | Swanson et al. |
| 2003/0204138 A1 | 10/2003 | Choi |
| 2003/0216792 A1 | 11/2003 | Levin et al. |
| 2003/0216794 A1 | 11/2003 | Becker et al. |
| 2003/0225331 A1 | 12/2003 | Diederich et al. |
| 2003/0236443 A1 | 12/2003 | Cespedes et al. |
| 2003/0236539 A1 | 12/2003 | Rabiner et al. |
| 2004/0010289 A1 | 1/2004 | Biggs et al. |
| 2004/0044286 A1 | 3/2004 | Hossack et al. |
| 2004/0054362 A1 | 3/2004 | Lopath et al. |
| 2004/0064090 A1 | 4/2004 | Keren et al. |
| 2004/0064091 A1 | 4/2004 | Keren et al. |
| 2004/0068257 A1 | 4/2004 | Lopath et al. |
| 2004/0082859 A1 | 4/2004 | Schaer |
| 2004/0097996 A1 | 5/2004 | Rabiner et al. |
| 2004/0101523 A1 | 5/2004 | Reitz et al. |
| 2004/0127942 A1 | 7/2004 | Yomtov et al. |
| 2004/0158151 A1 | 8/2004 | Ranucci et al. |
| 2004/0162590 A1 | 8/2004 | Whitehurst et al. |
| 2004/0176699 A1 | 9/2004 | Walker et al. |
| 2004/0176757 A1 | 9/2004 | Sinelnikov et al. |
| 2004/0215186 A1 | 10/2004 | Cornelius et al. |
| 2004/0243102 A1 | 12/2004 | Berg et al. |
| 2004/0243206 A1 | 12/2004 | Tadlock |
| 2004/0249416 A1 | 12/2004 | Yun et al. |
| 2004/0260278 A1 | 12/2004 | Anderson et al. |
| 2005/0010263 A1 | 1/2005 | Schauerte |
| 2005/0010270 A1 | 1/2005 | Laufer |
| 2005/0080409 A1 | 4/2005 | Young et al. |
| 2005/0080459 A1 | 4/2005 | Jacobson et al. |
| 2005/0153885 A1 | 7/2005 | Yun et al. |
| 2005/0165391 A1 | 7/2005 | Maguire et al. |
| 2005/0171524 A1* | 8/2005 | Stern et al. ............ 606/41 |
| 2005/0171575 A1 | 8/2005 | Dev et al. |
| 2005/0187579 A1 | 8/2005 | Danek et al. |
| 2005/0192638 A1 | 9/2005 | Gelfand et al. |
| 2005/0209548 A1 | 9/2005 | Dev et al. |
| 2005/0209588 A1 | 9/2005 | Larson et al. |
| 2005/0209642 A1 | 9/2005 | Palti |
| 2005/0215949 A1* | 9/2005 | Bertolero et al. ........ 604/102.03 |
| 2005/0228459 A1 | 10/2005 | Levin et al. |
| 2005/0240170 A1 | 10/2005 | Zhang et al. |
| 2005/0240241 A1 | 10/2005 | Yun et al. |
| 2005/0245892 A1 | 11/2005 | Elkins et al. |
| 2005/0251127 A1 | 11/2005 | Brosch et al. |
| 2005/0288730 A1 | 12/2005 | Deem et al. |
| 2006/0009753 A1 | 1/2006 | Fjield et al. |
| 2006/0025821 A1 | 2/2006 | Gelfand et al. |
| 2006/0041277 A1 | 2/2006 | Deem et al. |
| 2006/0057560 A1 | 3/2006 | Hlavka et al. |
| 2006/0058711 A1 | 3/2006 | Harhen et al. |
| 2006/0064081 A1 | 3/2006 | Rosinko |
| 2006/0088705 A1 | 4/2006 | Mitsumori |
| 2006/0089674 A1 | 4/2006 | Walters et al. |
| 2006/0095029 A1 | 5/2006 | Young et al. |
| 2006/0100514 A1 | 5/2006 | Lopath |
| 2006/0100667 A1 | 5/2006 | Machado et al. |
| 2006/0106429 A1 | 5/2006 | Libbus et al. |
| 2006/0111754 A1 | 5/2006 | Rezai et al. |
| 2006/0116720 A1 | 6/2006 | Knoblich |
| 2006/0121016 A1 | 6/2006 | Lee |
| 2006/0121610 A1 | 6/2006 | Rubinsky et al. |
| 2006/0135998 A1 | 6/2006 | Libbus et al. |
| 2006/0136004 A1 | 6/2006 | Cowan et al. |
| 2006/0142801 A1 | 6/2006 | Demarais et al. |
| 2006/0149350 A1 | 7/2006 | Patel et al. |
| 2006/0155344 A1 | 7/2006 | Rezai et al. |
| 2006/0167437 A1 | 7/2006 | Valencia |
| 2006/0167498 A1 | 7/2006 | DiLorenzo |
| 2006/0167499 A1 | 7/2006 | Palti |
| 2006/0189941 A1 | 8/2006 | Seward et al. |
| 2006/0189960 A1 | 8/2006 | Kesten et al. |
| 2006/0190044 A1 | 8/2006 | Libbus et al. |
| 2006/0206028 A1 | 9/2006 | Lee et al. |
| 2006/0206149 A1 | 9/2006 | Yun |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0229594 A1 | 10/2006 | Francischello et al. |
| 2006/0229677 A1 | 10/2006 | Moffit et al. |

(56) References Cited

U.S. PATENT DOCUMENTS

| | | |
|---|---|---|
| 2006/0235474 A1 | 10/2006 | Demarais |
| 2006/0241524 A1 | 10/2006 | Lee et al. |
| 2006/0265014 A1 | 11/2006 | Demarais et al. |
| 2006/0265015 A1 | 11/2006 | Demarais et al. |
| 2006/0270975 A1 | 11/2006 | Savage |
| 2006/0270976 A1 | 11/2006 | Savage et al. |
| 2006/0271111 A1 | 11/2006 | Demarais et al. |
| 2006/0276852 A1 | 12/2006 | Demarais et al. |
| 2007/0066957 A1 | 3/2007 | Demarais et al. |
| 2007/0066972 A1 | 3/2007 | Ormsby et al. |
| 2007/0083239 A1 | 4/2007 | Demarais et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0142864 A1 | 6/2007 | Libbus et al. |
| 2007/0156200 A1 | 7/2007 | Kornet et al. |
| 2007/0173899 A1 | 7/2007 | Levin et al. |
| 2007/0203546 A1 | 8/2007 | Stone et al. |
| 2007/0203549 A1 | 8/2007 | Demarais et al. |
| 2007/0208382 A1 | 9/2007 | Yun |
| 2007/0244479 A1 | 10/2007 | Beatty et al. |
| 2007/0249046 A1 | 10/2007 | Shields |
| 2007/0265687 A1 | 11/2007 | Deem et al. |
| 2007/0282376 A1 | 12/2007 | Shuros et al. |
| 2007/0282407 A1 | 12/2007 | Clark |
| 2007/0288070 A1 | 12/2007 | Libbus et al. |
| 2008/0004673 A1 | 1/2008 | Rossing et al. |
| 2008/0015659 A1 | 1/2008 | Zhang et al. |
| 2008/0027505 A1 | 1/2008 | Levin et al. |
| 2008/0039904 A1 | 2/2008 | Bulkes et al. |
| 2008/0086073 A1* | 4/2008 | McDaniel ............... 604/22 |
| 2008/0091255 A1 | 4/2008 | Caparso et al. |
| 2008/0108988 A1* | 5/2008 | Edwards ............... 606/41 |
| 2008/0140150 A1 | 6/2008 | Zhou et al. |
| 2008/0172049 A1 | 7/2008 | Bredno et al. |
| 2008/0172104 A1 | 7/2008 | Kieval et al. |
| 2008/0195092 A1 | 8/2008 | Kim et al. |
| 2008/0213331 A1 | 9/2008 | Gelfand et al. |
| 2008/0255478 A1 | 10/2008 | Burdette |
| 2008/0255642 A1 | 10/2008 | Zarins et al. |
| 2008/0300588 A1 | 12/2008 | Groth et al. |
| 2008/0319513 A1 | 12/2008 | Pu et al. |
| 2009/0024195 A1 | 1/2009 | Rezai et al. |
| 2009/0036948 A1 | 2/2009 | Levin et al. |
| 2009/0062697 A1 | 3/2009 | Zhang et al. |
| 2009/0062873 A1 | 3/2009 | Wu et al. |
| 2009/0076409 A1 | 3/2009 | Wu et al. |
| 2009/0124964 A1 | 5/2009 | Leach et al. |
| 2009/0198223 A1 | 8/2009 | Thilwind et al. |
| 2009/0216286 A1 | 8/2009 | DiLorenzo |
| 2009/0221939 A1 | 9/2009 | Demarais et al. |
| 2009/0248011 A1 | 10/2009 | Hlavka et al. |
| 2009/0306739 A1 | 12/2009 | DiLorenzo |
| 2010/0004528 A1 | 1/2010 | Weiss et al. |
| 2010/0010567 A1 | 1/2010 | Deem et al. |
| 2010/0016934 A1 | 1/2010 | David et al. |
| 2010/0037902 A1 | 2/2010 | Wirtz et al. |
| 2010/0041977 A1 | 2/2010 | Lips et al. |
| 2010/0057150 A1 | 3/2010 | Demarais et al. |
| 2010/0063492 A1 | 3/2010 | Kahlert et al. |
| 2010/0130892 A1 | 5/2010 | Warnking |
| 2010/0137860 A1 | 6/2010 | Demarais et al. |
| 2010/0137952 A1 | 6/2010 | Demarais et al. |
| 2010/0168731 A1 | 7/2010 | Wu et al. |
| 2010/0168737 A1 | 7/2010 | Grunewald |
| 2010/0168739 A1 | 7/2010 | Wu et al. |
| 2010/0171394 A1 | 7/2010 | Glenn et al. |
| 2010/0174282 A1 | 7/2010 | Demarais et al. |
| 2010/0185126 A1 | 7/2010 | Hall et al. |
| 2010/0191112 A1 | 7/2010 | Demarais et al. |
| 2010/0211131 A1 | 8/2010 | Williams et al. |
| 2010/0222851 A1 | 9/2010 | Deem et al. |
| 2010/0222854 A1 | 9/2010 | Demarais et al. |
| 2010/0249773 A1 | 9/2010 | Clark et al. |
| 2010/0249859 A1 | 9/2010 | DiLorenzo |
| 2010/0249888 A1 | 9/2010 | Glenn et al. |
| 2010/0259832 A1 | 10/2010 | Suijver et al. |
| 2010/0262130 A1 | 10/2010 | Mihajlovic et al. |
| 2010/0268307 A1 | 10/2010 | Demarais et al. |
| 2010/0272398 A1 | 10/2010 | Mihajlovic et al. |
| 2010/0274235 A1 | 10/2010 | Mihajlovic et al. |
| 2010/0280504 A1 | 11/2010 | Manzke et al. |
| 2010/0290318 A1 | 11/2010 | Kuiper et al. |
| 2011/0004184 A1 | 1/2011 | Proksch et al. |
| 2011/0028798 A1 | 2/2011 | Hyde et al. |
| 2011/0029038 A1 | 2/2011 | Hyde et al. |
| 2011/0029044 A1 | 2/2011 | Hyde et al. |
| 2011/0060324 A1 | 3/2011 | Wu et al. |
| 2011/0079230 A1 | 4/2011 | Danek et al. |
| 2011/0086257 A1 | 4/2011 | Pitteloud et al. |
| 2011/0104060 A1 | 5/2011 | Seward |
| 2011/0104061 A1 | 5/2011 | Seward |
| 2011/0112400 A1 | 5/2011 | Emery et al. |
| 2011/0118598 A1 | 5/2011 | Gertner |
| 2011/0118632 A1 | 5/2011 | Sinelnikov et al. |
| 2011/0118714 A1 | 5/2011 | Deladi et al. |
| 2011/0118725 A1 | 5/2011 | Mayse et al. |
| 2011/0130663 A1 | 6/2011 | Raju et al. |
| 2011/0137298 A1 | 6/2011 | Nguyen et al. |
| 2011/0163630 A1 | 7/2011 | Klootwijk et al. |
| 2011/0166482 A1 | 7/2011 | Stack et al. |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208173 A1 | 8/2011 | Sobotka et al. |
| 2011/0208175 A1 | 8/2011 | Sobotka et al. |
| 2011/0237983 A1 | 9/2011 | Nita et al. |
| 2011/0257512 A1 | 10/2011 | Krueger |
| 2011/0257523 A1 | 10/2011 | Hastings et al. |
| 2011/0257561 A1 | 10/2011 | Gertner et al. |
| 2011/0257564 A1 | 10/2011 | Demarais et al. |
| 2011/0257641 A1 | 10/2011 | Hastings et al. |
| 2011/0257647 A1 | 10/2011 | Mayse et al. |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0270238 A1 | 11/2011 | Rizq et al. |
| 2011/0275962 A1 | 11/2011 | Deladi et al. |
| 2011/0301508 A1 | 12/2011 | Sethuraman et al. |
| 2011/0301662 A1 | 12/2011 | Bar-Yoseph et al. |
| 2011/0307034 A1 | 12/2011 | Hastings et al. |
| 2011/0313290 A1 | 12/2011 | Weekamp et al. |
| 2011/0319765 A1 | 12/2011 | Gertner et al. |
| 2012/0004547 A1 | 1/2012 | Harks et al. |
| 2012/0004656 A1 | 1/2012 | Jackson et al. |
| 2012/0016358 A1 | 1/2012 | Mayse et al. |
| 2012/0022409 A1 | 1/2012 | Gertner et al. |
| 2012/0029509 A1 | 2/2012 | Smith |
| 2012/0059286 A1 | 3/2012 | Hastings et al. |
| 2012/0059431 A1 | 3/2012 | Williams et al. |
| 2012/0065492 A1 | 3/2012 | Gertner et al. |
| 2012/0065493 A1 | 3/2012 | Gertner |
| 2012/0065494 A1 | 3/2012 | Gertner et al. |
| 2012/0065506 A1 | 3/2012 | Smith |
| 2012/0065554 A1 | 3/2012 | Pikus |
| 2012/0078278 A1 | 3/2012 | Bales, Jr. et al. |
| 2012/0089047 A1 | 4/2012 | Ryba et al. |
| 2012/0109018 A1 | 5/2012 | Gertner et al. |
| 2012/0109021 A1 | 5/2012 | Hastings et al. |
| 2012/0116392 A1 | 5/2012 | Willard |
| 2012/0123243 A1 | 5/2012 | Hastings |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0215106 A1 | 8/2012 | Sverdlik et al. |
| 2013/0075928 A1 | 3/2013 | Gallegos et al. |

FOREIGN PATENT DOCUMENTS

| | | |
|---|---|---|
| EP | 0 838 980 | 4/1998 |
| EP | 1042990 | 10/2000 |
| EP | 1384445 | 1/2004 |

(56) References Cited

FOREIGN PATENT DOCUMENTS

| | | |
|---|---|---|
| EP | 1598024 | 11/2005 |
| EP | 2092957 | 8/2009 |
| EP | 2 218 479 | 8/2010 |
| GB | 2 037 166 | 7/1980 |
| JP | 07-178173 | 7/1995 |
| JP | 10-127678 | 5/1998 |
| JP | 11-218100 | 8/1999 |
| JP | 200 054153 | 2/2000 |
| JP | 2002-078809 | 3/2002 |
| WO | WO 90/00420 | 1/1990 |
| WO | WO 92/07622 | 5/1992 |
| WO | WO 92/20291 | 11/1992 |
| WO | WO 94/05365 | 3/1994 |
| WO | WO 94/11057 | 5/1994 |
| WO | WO 95/19143 | 7/1995 |
| WO | WO 95/25472 | 9/1995 |
| WO | WO 96/00039 | 1/1996 |
| WO | WO 97/13463 | 4/1997 |
| WO | WO 97/36548 | 10/1997 |
| WO | WO 98/41178 | 9/1998 |
| WO | WO 98/42403 | 10/1998 |
| WO | WO 98/49957 | 11/1998 |
| WO | WO 98/52465 | 11/1998 |
| WO | WO 99/02096 | 1/1999 |
| WO | WO 99/35987 | 7/1999 |
| WO | WO 99/44519 | 9/1999 |
| WO | WO 99/44523 | 9/1999 |
| WO | WO 99/52423 | 10/1999 |
| WO | WO 99/56812 | 11/1999 |
| WO | WO 00/16850 | 3/2000 |
| WO | WO 00/27292 | 5/2000 |
| WO | WO 00/42934 | 7/2000 |
| WO | WO 00/45706 | 8/2000 |
| WO | WO 00/51511 | 9/2000 |
| WO | WO 00/51683 | 9/2000 |
| WO | WO 00/56237 | 9/2000 |
| WO | WO 00/57495 | 9/2000 |
| WO | WO 00/67648 | 11/2000 |
| WO | WO 00/67656 | 11/2000 |
| WO | WO 00/67830 | 11/2000 |
| WO | WO 00/67832 | 11/2000 |
| WO | WO 01/13357 | 2/2001 |
| WO | WO 01/22897 | 4/2001 |
| WO | WO 01/22897 A1 | 4/2001 |
| WO | WO 01/70114 | 9/2001 |
| WO | WO 01/80723 A2 | 11/2001 |
| WO | WO 01/82814 | 11/2001 |
| WO | WO 01/37925 | 12/2001 |
| WO | WO 02/05868 | 1/2002 |
| WO | WO 01/80723 A3 | 4/2002 |
| WO | WO 02/083196 | 10/2002 |
| WO | WO 02/085192 | 10/2002 |
| WO | WO 03/003930 | 1/2003 |
| WO | WO 03/007649 | 1/2003 |
| WO | WO 2004/23978 | 3/2004 |
| WO | WO 2005/009218 | 2/2005 |
| WO | WO 2005/032646 | 4/2005 |
| WO | WO 2005/041748 A2 | 5/2005 |
| WO | WO 2005/110528 | 11/2005 |
| WO | WO 2006/022790 | 3/2006 |
| WO | WO 2006/0041847 | 4/2006 |
| WO | WO 2006/0041881 | 4/2006 |
| WO | WO 2007/008954 | 1/2007 |
| WO | WO 2007/035537 | 3/2007 |
| WO | WO 2007/078997 | 7/2007 |
| WO | WO 2007/086965 | 8/2007 |
| WO | WO 2007/103879 | 9/2007 |
| WO | WO 2007/103881 | 9/2007 |
| WO | WO 2007/121309 | 10/2007 |
| WO | WO 2007/124458 | 11/2007 |
| WO | WO 2007/146834 | 12/2007 |
| WO | WO 2008/003058 | 1/2008 |
| WO | WO 2008/052186 | 5/2008 |
| WO | WO 2008/061150 | 5/2008 |
| WO | WO 2008/061152 | 5/2008 |
| WO | WO 2008/070413 | 10/2008 |
| WO | WO 2008/151001 | 12/2008 |
| WO | WO 2009/149315 | 12/2009 |
| WO | WO 2010/033940 | 3/2010 |
| WO | WO 2010/067360 | 6/2010 |
| WO | WO 2010/078175 | 8/2010 |
| WO | WO 2011/088399 | 1/2011 |
| WO | WO 2011/024133 | 3/2011 |
| WO | WO 2011/046880 | 4/2011 |
| WO | WO 2011/051872 | 5/2011 |
| WO | WO 2011/053757 | 5/2011 |
| WO | WO 2011/053772 | 5/2011 |
| WO | WO 2011/059792 | 5/2011 |
| WO | WO 2011/060200 | 5/2011 |
| WO | WO 2011/060201 | 5/2011 |
| WO | WO 2011/080666 | 7/2011 |
| WO | WO 2011/082279 | 7/2011 |
| WO | WO 2011/094367 | 8/2011 |
| WO | WO 2011/101778 | 8/2011 |
| WO | WO 2011/139589 | 11/2011 |
| WO | WO 2012/001595 | 1/2012 |
| WO | WO 2012/025245 | 3/2012 |
| WO | WO 2012/068354 | 5/2012 |
| WO | WO 2012/112165 | 8/2012 |

OTHER PUBLICATIONS

Written Opinion of the International Searching Authority for PCT/US2010/020333, mailed Feb. 25, 2010, 7 pages.

Response to Written Opinion under Article 34 for PCT/US2010/020333, filed Nov. 8, 2010, 13 pages.

Arruda, M. S., et al. "Development and validation of an ECG algorithm for identifying aecessory pathway ablation site in Wolff-ParkinsonWhite syndrome." J Cardiovasc Electrophysiol, 9:2-12 (1998).

Avitall, B., et al. "The creation of linear continuous lesions in the atria with an expandable loop catheter." J Am Coll Cardiol, 33,4:972-984 (1999).

Bartlett, T. G., et al. "Current management of the Wolff-Parkinson-White syndrome." J Card Surg, 8:503-515 (1993).

Benito, F., et al. "Radio frequency catheter ablation of accessory pathways in infants," Heart, 78: 160-162 (1997).

Blumenfeld, J. D., et al. "α-Adrenergic receptor blockade as a therapeutic approach for suppressing the renin-angiotensin-aldosterone system in norrnotensive and hypertensive subjects." AJH, 12:451-459 (1999).

Callans, D. J. "Narrowing of the superior vena cava—right atrium junction during radiofrequency catheter ablation for inappropriate sinus tachycardia: Analysis with intracardiac echocardiography." JACC, 33:1667-1670 (1999).

Cao, H. et al. "Flow effect on lesion formation in RF cardiac catheter ablation." IEEE T Bio-Med Eng, 48:425-433 (2001).

Chen, S.-A., et al. "Complications of diagnostic electrophysiologic studies and radiofrequency catheter ablation in patients with tachyarrhythmias: An eight-year survey of 3,966 consecutive procedures in a tertiary referral center." Am J Cardiol, 77 :41-46 (1996).

Cioni, R., et al. "Renal artery stenting in patients with a solitary functioning kidney." Cardiovasc Intervent Radiol, 24:372-377 (2001).

Cosby, R. L., et al. "The role of the sympathetic nervous system and vasopressin in the pathogenesis of the abnormal sodium and water." *Nefrologia*, V, 4:271-277 (1985).

Cox, J. L. "The status of surgery for cardiac arrhythmias." Circulation, 71 :413-417 (1985).

Cox J. L. et al. "Five-year experience with the Maze procedure for atrial fibrillation." Ann Thorac Surg, 56:814-824 (1993).

Cruickshank, J. M. "Beta-blockers continue to surprise us." Eur Heart J, 21:354-364 (2000).

Curtis, J. J., et al. "Surgical therapy for persistent hypertension after renal transplantation," Transplantation, 31:125-128 (1981).

Demazumder, D., et al. "Comparison of irrigated electrode designs for radiofrequency ablation of myocardium." J Intent Card Electr, 5:391-400 (2001).

(56) References Cited

OTHER PUBLICATIONS

DiBona, G. F. "Neural control of the kidney: Functionally specific renal sympathetic nerve fibers." Am J Physiol Regulatory Integrative Comp Physiol, 279:R1517-R1524 (2000).
DiBona, G. F. "Sympathetic nervous system and kidney in hypertension," Nephrol and Hypertension, 11: 197-200 (2002).
DiBona, G. F., et al. "Neural control of renal function," Physiol Rev, 77:75-197 (1997).
DiBona, G. F., et al. "Renal hemodynamic effects of activation of specific renal sympathetic nerve fiber groups." Am J Physiol Regul Integr Comp Physiol, 276:R539-R549 (1999).
Doggrell, S. A., et al. "Rat models of hypertension, cardiac hypertrophy and failure." Cardiovasc Res, 39:89-105 (1998).
Dong, Q., et al. "Diagnosis ofrenal vascular disease with MR angiography." RadioGraphies, 19:1535-1554 (1999).
Dubuc, M., et al. "Feasibility of cardiac cryoablation using a transvenous steerable electrode catheter," J Intent Cardiac Electrophysiol, 2:285-292 (1998).
Gilard, M., et al. "Angiographic anatomy of the coronary sinus and its tributaries." PACE, 21:2280-2284 (1998).
Goriseh, W., et al. "Heat-induced contraction of blood vessels." Lasers Surg Med, 2:1-13 (1982).
Haines, D. E., et al. "Tissue heating during radiofrequeney catheter ablation; a thermodynamic model and observations in isolated perfused and superfused canine right ventrieular free wall." PACE, 12:962-976 (1989).
Han, Y-M. et al. "Renal artery embolization with diluted hot contrast medium: An experimental study," J Vasc Intent Radiol, 12:862-868 (2001).
Hansen, J. M., et al. "The transplanted human kidney does not achieve functional reinnervation." Clin Sci, 87, 1: 13-20 (1994).
Hindricks, G. "The Multicentre European Radiofrequency Survey (MERFS): Complications of radiofrequency catheter ablation of arrhythmias." Eur Heart J, 14:1644-1653 (1993).
Ho, S. Y., et al. "Architecture of the pulmonary veins: Relevance to radiofrequency ablation." Heart, 86:265-270 (2001).
Huang et al., "Renal denervation prevents and reverses hyperinsulinemia-induced hypertension in rats," Hypertension 32, pp. 249-254 (1998).
Huang, S. K. S., et al. "Radiofrequency catheter ablation of cardiac arrhythmias: Basic concepts and clinical applications." 2nd ed. Armonk, NY: Futura Publishing Co. (2000).
Jackman, W. M., et al. "Treatment of supraventricular tachycardia due to atrioventricular nodal reentry by radiofrequency catheter ablation of slow-pathway conduction." N England J Med, 327, 5:313-318 (Jul. 30, 1992).
Jain, M. K., et al. "A three-dimensional finite element model of radiofrequency ablation with blood flow and its experimental validation." Ann Biomed Eng, 28:1075-1084 (2000).
Janssen, B. J. A., et al. "Renal nerves in hypertension." Miner Electrolyte Metab, 15:74-82 (1989).
Kapural, L., et al. "Radiofrequency ablation for chronic pain control." Curr Pain Headache Rep, 5:517-525 (2001).
Koepke, J. P., et al. "The physiology teacher: Functions ofthe renal nerves." The Physiologist, 28, 1 :47-52 (1985).
Kompanowska, E., et al. "Early effects of renal denervation in the anaesthetised rat: Natriuresis and increased cortical blood flow," J Physiol, 531.2:527-534 (2001).
Labonte, S. "Numerieal model for radio-frequency ablation of the endocardium and its experimental validation." IEEE T Bio-med Eng, 41,2:108-115 (1994).
Lee, S.-J., et al. "Ultrasonic energy in endoscopic surgery," Yonsei Med J, 40:545-549 (1999).
Leertouwer, T. c., et al. "In-vitro validation, with histology, of intravascular ultrasound in renal arteries." J Hypertens, 17:271-277 (1999).
Lesh, M.D., "An Anatomic Approach to Prevention of Atrial Fibrillation: Pulmonary Vein Isolation with Through-the-Balloon Ultrasound Ablation (TTB-US)," Thorac. Cardiovasc. Surg. 47 (1999) (Suppl.) 347-51.

Lowe, J. E. "Surgical treatment of the Wolff-Parkinson-White syndrome and other supraventricular tachyarrhythmias." J Card Surg, 1 :117-134 (1986).
Lundin, S. et al. "Renal sympathetic activity in spontaneously hypertensive rats and normotensive controls, as studied by three different methods." Acta Physiol Scand, 120,2:265-272 (1984).
Lustgarten, D. L., et al. "Cryothermal ablation: Mechanism of tissue injury and current experience in the treatment of tachyarrhythmias," Progr Cardiovasc Dis, 41:481-498 (1999).
McRury I. D., et al. "Nonunifonn heating during radiofrequency catheter ablation with long electrodes." Circulation, 96:4057-4064 (1997).
Mehdirad, A., et al. "Temperature controlled RF ablation in canine ventricle and coronary sinus using 7 Fr or 5 Fr ablation electrodes." PACE, 21:310-321 (1998).
Miller, B. F., and Keane, C. B. "Miller-Keane Encyclopedia & Dictionary 0/ Medicine, Nursing, & Allied Health." Philadelphia: Saunders (1997) ("ablation").
Misaki, T., et al. "Surgical treatment of patients with Wolff-ParkinsonWhite syndrome and associated Ebstein's anomaly." J Thorae Cardiovase Surg, 110: 1702-1707 (1995).
Moak, J. P., et al. "Case report: Pulmonary vein stenosis following RF ablation of paroxysmal atrial fibrillation: Successful treatment with balloon dilation." J Intery Card Electrophys, 4:621-631 (2000).
Morrissey, D. M., "Sympathectomy in the treatment of hypertension." Lancet, CCLVIX:403-408 (1953).
Nakagawa, H., et al. "Comparison of in vivo tissue temperature profile and lesion geometry for radiofrequeney ablation with a saline-irrigated electrode versus temperature control in a eanine thigh muscle preparation." Circulation, 91 :2264-2273 (1995).
Nakagawa, H., et al. "Inverse relationship between electrode size and lesion size during radiofrequency ablation with active electrode cooling." Circulation, 98:458-465 (1998).
Nakagawa, A., et al. "Selective ablation of porcine and rabbit liver tissue using radiofrequency: Preclinical study." Eur Surg Res, 31: 371-379 (1999).
Neutel, J. M. "Hypertension and its management: A problem in need of new treatment strategies." JRAAS, I:S 1 O-S 13 (2000).
Nozawa, T., et al. "Effects of long-term renal sympathetic denervation on heart failure after myocardial infarction in rats." Heart Vessels, 16:51-56 (2002).
O'Connor, B. K., et al. "Radiofrequeney ablation of a posteroseptal accessory pathway via the middle cardiac vein in a six-year-old child." PACE, 20:2504-2507 (1997).
Oliveira et al., "Renal Denervation Normalizes Pressure and Baroreceptor Reflex in High Renin Hypertension in Conscious Rats," Hypertension Suppl. II vol. 19 No. 2, pp. 17-21 (1992).
Oral, H., et al. "Pulmonary vein isolation for paroxysmal and persistent atrial fibrillation." Circulation, 105: 1077-1081 (2002).
Page, I., et al. "The effect of renal denervation on the level of arterial blood pressure and renal function in essential hypertension." J Clin Invest, XIV:27-30 (1935).
Panescu, D., et al. "Radiofrequency multielectrode catheter ablation in the atrium." Phys Med Biol, 44:899-915 (1999).
Pavin, D., et al. "Permanent left atrial tachyeardia: Radiofrequency catheter ablation through the eoronary sinus." J Cardiovasc Electrophysiol, 12:395-398 (2002).
Peet, M., "Hypertension and its surgical treatment by bilateral supradiaphragmatic splanchnicectomy," Am. J. Surgery, pp. 48-68 (1948).
Petersen, H. H., et al. "Lesion dimensions during temperature controlled radiofrequency catheter ablation of left ventricular porcine myocardium: Impact of ablation site, electrode size, and convective cooling." Circulation, 99:319-325 (1999).
Pohl, M.A. "Renovaseular hypertension and isehemie nephropathy" A chapter in a book edited by Sehrier, R. W. "Atlas of diseases of the kidney: Hypertension and the kidney." Blackwell Science (1999).
Pugsley, M. K., et al. "The vascular system: An overview of structure and function." J Pharmacol Toxical Methods, 44:333-340 (2000).
Sanderson, J. E. et al. "Effect of B-blockage on baroreceptor and autonomic function in heart failure." Clin Sei, 69:137-146 (1999).

(56) References Cited

OTHER PUBLICATIONS

Schauerte, P. et al. "Catheter ablation of cardiac autonomic nerves for prevention of vagal atrial fibrillation," Circulation, 102:2774-2780 (2000).
Scheinman, M. M., et al. "The 1998 NASPE prospective catheter ablation registry." PACE, 23:1020-1028 (2000).
Smithwick et al., "Splanchnicectomy for Essential Hypertension," J. Am. Med. Assn. 152:16, pp. 1501-1504 (1953).
Solis-Herruzo et al., "Effects of Lumbar Sympathetic Block on Kidney Function in Cirrhotic Patients with Hepatorenal Syndrome," J. Hepatol. 5, pp. 167-173 (1987).
Stella A., et al. "Effects of reversible renal denervation on haemodynamic and excretory functions of the ipsilateral and contralateral kidney in the cat," J Hypertension, 4: 181-188 (1986).
Stellbrink, C., et al. "Transcoronary venous radiofrequency catheter ablation ofventricular tachyeardia." J Cardiovasc Electrophysiol, 8:916-921 (1997).
Swain, et al. Gastrointestial Endoscopy. 1994; 40:AB35.
Takahashi, H., et al. "Retardation of the development of hypertension in DOCA-salt rats by renal denervation." Jpn Circ J, 48:567-574 (1984).
Tungjitkusolmun, S. "Ablation." A chapter in a book edited by Webster, J. G., "Minimally invasive medical technology." Bristol UK: IOP Publishing, 219 (2001).
Uchida, F., et al. "Effect of radio frequency catheter ablation on parasympathetic denervation: A comparison of three different ablation sites," PACE, 21:2517-2521 (1998).
Uflacker, R., "Atlas of vascular anatomy: An angiographic approach. "Baltimore: Williams & Wilkins, 424 (1997).
Valente, J. F. "Laparoscopic renal denervation for intractable ADPKD-related pain," Nephrol Dial Transplant, 16:160 (2001).
Van Hare, G. F., et al. "Percutaneous radiofrequency catheter ablation for supraventricular arrhythmias in children." JACC, 17:1613-1620 (1991).
Vujaskovie, Z., et al. "Effects of intraoperative hyperthermia on canine seiatie nerve: Histopathologie and morphometric studies." Int J Hyperthermia, 10,6:845-855 (1994).
Weinstock, M., et al. "Renal denervation prevents sodium retention and hypertension in salt-sensitive rabbits with genetic baroreflex impairment," Clinical Science, 90:287-293 (1996).
Weir, M. R., et al. "The renin-angiotensin-aldosterone system: A specific target for hypertension management." Am J Hypertens, 12:205S-213S (1999).
Yamamoto, T., et al. "Blood velocity profiles in the human renal artery by Doppler ultrasound and their relationship to atherosclerosis. "Arterioscl Throm Vas, 16: 172-177 (1996).
Extended European Search Report, Application No. EP 10 72 9496, mailed Jul. 12, 2012.
Partial Supplementary European Search Report, Application No. EP 01 95 2750, Filed Sep. 16, 2005.
U.S. Appl. No. 60/236,420, filed Sep. 28, 2000, Harrison et al.
U.S. Appl. No. 60/370,190, filed Apr. 8, 2002, Levin et al.
U.S. Appl. No. 60/415,575, filed Oct. 3, 2002, Levin et al.
U.S. Appl. No. 60/442,970, filed Jan. 29, 2003, Gelfand et al.
U.S. Appl. No. 60/258,824, filed Nov. 6, 2009, Gelfand et al.
Diederich, C. J. et al., Transurethral ultrasound array for prostate thermal therapy: initial studies, Ieee Transactions on Ultrasonics, Ferroelectrics and Frequency Control Ieee USA, vol. 43, No. 6, Nov. 1996, pp. 1011-1022, XP002717467, USA ISSN: 0885-3010.
Chen, Shih-Ann, M.D., "Initiation of Atrial Fibrillation by Ectopic Beats Originating From the Pulmonary Veins," Circulation 100(18):1879-86, 1999.
Chinitz, Larry A., "Mapping Reentry Around Atriotomy Scars Using Double Potentials," 1996.
Cosio, Francisco G., "Atrial Flutter Mapping and Ablation II," Pacing & Clin. Electrophysiol. 19(6):965-75, 1996.
Feld, Gregory K., "Radiofrequency Catheter Ablation for the Treatment of Human Type I Atrial Flutter," 1992.
Fjield, et al., U.S. Appl. No. 60/218,641, filed Jul. 13, 2000.

Gallagher, John J., "Wolff-Parkinson-White Syndrome: Surgery to Radiofrequency Catheter Ablation," 1997.
Haissaguerre, Michel, "Electrophysiological End Point for Catheter Ablation of Atrial Fibrillation Initiated From Multiple Venous Foci," 1999.
Haissaguerre, Michel, M.D., "Predominant Origin of Atrial Panarrythmic Triggers in the Pulmonary Veins: A Distinct Electrophysiologic Entity," 1997.
Haissaguerre, Michel, M.D., "Radiofrequency Catheter Ablation in Unusual Mechanisms of Atrial Fibrillation," 1994.
Haissaguerre, Michel, M.D., "Right and Left Atrial Radiofrequency Catheter Therapy of Paroxysmal Atrial Fibrillation," 1996.
Haissaguerre, Michel, M.D., "Spontaneous Initiation of Atrial Fibrillation by Ectopic Beats Originating in the Pulmonary Veins," 1998.
Hatala, Robert, "Radiofrequency Catheter Ablation of Left Atrial Tachycardia Originating Within the Pulmonary Vein in a Patient with Dextrocardia," 1996.
Hocini, Meleze, "Concealed Left Pulmonary Vein Potentials Unmasked by Left Atrial Stimulation," 2000.
Hocini, Meleze, "Multiple Sources Initating Atrial Fibrillation from a Single Pulmonary Vein Identified by a Circumferential Catheter," 2000.
Hsieh, Ming-Hsiung, M.D., "Double Multielectrode Mapping Catheters Facilitate Radiofrequency Catheter Ablation of Focal Atrial Fibrillation Originating from Pulmonary Veins," 1998.
Igawa, Osamu, "The Anatomical Features of the Junction between the Left Atrium and the Pulmonary Veins: the Relevance with Atrial Arrhythmia."
Jais, Pierre, M.D., "A Focal Source of Atrial Fibrillation Treated by Discrete Radiofrequency Ablation," 1996.
Kay, G. Neal, "Radiofrequency Ablation for Treatment of Primary Atrial Tachycardia," 1993.
Krimholtz et al., "New Equivalent Circuits for Elementary Piezoelectric Transducers," Electronics Lettres, vol. 6, No. 13, pp. 398-399, Jun. 25, 1970.
Kumagai, Koichiro, "Treatment of Mixed Atrial Fibrillation and Typical Atrial Flutter by Hybrid Catheter Ablation," 2000.
Lesh, M.D., "An Anatomic Approach to Prevention of Atrial Fibrillation: Pulmonary Vein Isolation with Through-the-Balloon Ultrasound Ablation (TTB-US)," Thorac. Cardiovasc. Surg. 47 (1999) (Suppl.) 34751.
Lesh, Michael D., M.D., "Radiofrequency Catheter Ablation of Atrial Arrhythmias," 1994.
Liem, L. Bing, "In Vitro and In Vivo Results of Transcatheter Microwave Ablation Using Forward-Firing Tip Antenna Design," 1996.
Lin, Wei-Shiang, M.D., "Pulmonary Vein Morphology in Patients with Paroxysmal Atrial Fibrillation Initiated by Ectopic Beats Originating From the Pulmonary Veins," Circulation 101(11):1274-81, 2000.
Mallavarapu, Christopher, "Radiofrequency Catheter Ablation of Atrial Tachycardia with Unusual Left Atrial Sites of Origin," 1996.
Montenero, Sandro, Annibale, "Electrograms for Identification of the Atrial Ablation Site During Catheter Ablation of Accessory Pathways," 1996.
Moubarak, Jean B., "Pulmonary Veins-Left Atrial Junction: Anatomic and Histological Study," Pacing & Clin. Electrophys. 23(11 pt. 2):1836-8, 2000.
O'Connor, Brian K., "Radiofrequency Ablation of a Posteroseptal Accessory Pathway Via the Middle Cardia Vein in a Six-Year Old Child," 1997.
Partial European Search Report, Application No. 10 01 0583, Sep. 28, 2011.
Partial European Search Report, Application No. 10 01 0582, Sep. 26, 2011.
International Search Report, Application No. PCT/US07/11346.
International Search Report, Application No. PCT/US2001/022221.
International Search Report, Application No. PCT/US01/22237.
International Search Report, Application No. PCT/US04/05197.
Supplementary European Search Report, Application No. EP 01 952 746.4, mailed Apr. 3, 2005.
Supplementary European Search Report, Application No. EP 07 77 6968, mailed Feb. 1, 2010.

(56) References Cited

OTHER PUBLICATIONS

Supplementary European Search Report, Application No. EP 01 952 750.6, mailed Dec. 13, 2005.
Prager, Nelson, A., "Long Term Effectiveness of Surgical Treatment of Ectopic Atrial Tachycardia," 1993.
Rappaport et al., "Wide-Aperture Microwave Catheter-Based Cardiac Ablation", Proceedings of the First Joint BMES/EMBS Conference, Oct. 13-16, 1999, p. 314.
Reuter, David, M.D., "Future Directions of Electrotherapy for Atrial Fibrillation," 1997.
Robbins, Ivan, M.D., "Pulmonary Vein Stenosis After Catheter Ablation of Atrial Fibrillation," 1998.
Scheinman, Melvin M., "NASPE Survey on Catheter Ablation," 1995.
Swartz, John F., "A Catheter-based Curative Approach to Atrial Fibrillation in Humans," 1994.
Swartz, John F., M.D., "Radiofrequency Endocardial Catheter Ablation of Accessory Atrioventricular Pathway Atrial Insertion Sites," 1993.
Tanaka et al., "A new radiofrequency thermal balloon catheter for pulmonary vein isolation," Journal of the American College of Cardiology 38(7): 2079-86, Dec. 2001.
Tracy, Cynthia M., "Radiofrequency Catheter Ablation of Ectopic Atrial Tachycardia Using Paced Activation Sequence Mapping," J. of the Amer. College of Cardiol. 21(4):910-7, 1993.
Van Hare, George F., "Radiofrequency Catheter Ablation of Supraventricular Arrhythmias in Patients With Congenital Heart Disease: Results and Technical Considerations," J. of the Amer. College of Cardiol. 22(3):883-90, 1993.
Volkmer, Marius, M.D., "Focal Atrial Tachycardia from Deep Inside the Pulmonary Veins," 1997.
Walsh, Edward P., M.D., "Transcatheter Ablation of Ectopic Atrial Tachycardia in Young Patients Using Radiofrequency Current," 1992.
Zhang et al., "The development of a RF electrical pole catheter for heart ablation," China Academic Journal Electronic Publishing House 23(5): 279-80, Sep. 1999.
Zipes, Douglas P., M.D., "Catheter Ablation of Arrhythmias," 1994.

\* cited by examiner

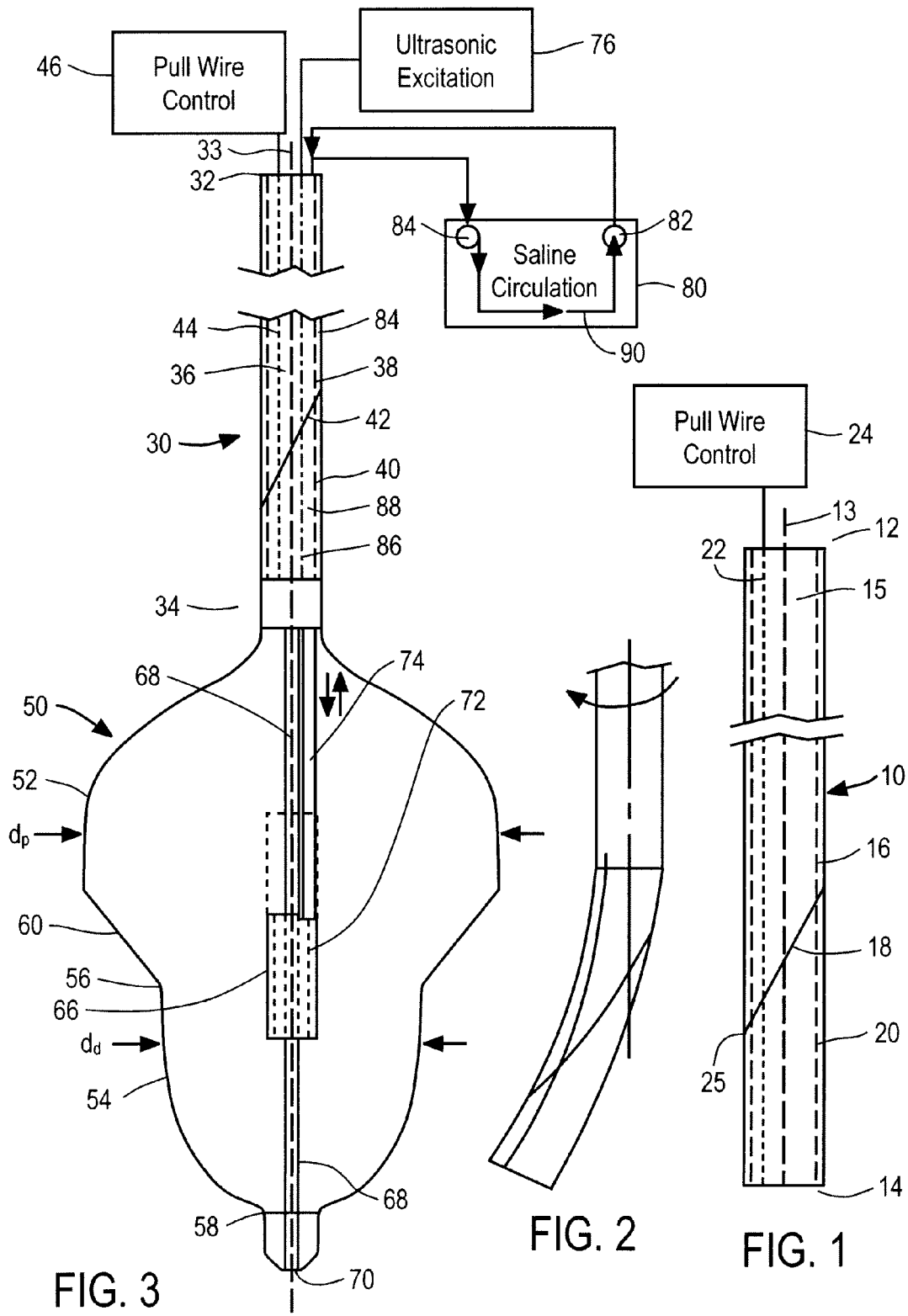

METHODS AND APPARATUS FOR TREATMENT OF CARDIAC VALVE INSUFFICIENCY

I. CROSS-REFERENCE TO RELATED APPLICATIONS

This application claims the benefit of U.S. Provisional Patent Application No. 61/204,744, filed Jan. 9, 2009 and entitled "Treatment of Mitral Valve Insufficiency," the entire contents of which are incorporated by reference herein.

I. BACKGROUND OF THE INVENTION

The present invention relates to treatment of cardiac valves in a mammalian subject.

Humans and other mammals have a four-chambered heart. Blood from the body flows into the right atrium, and from the right atrium through the tricuspid valve to right ventricle. The right ventricle pumps the blood through the pulmonary arteries to the lungs. Blood from the lungs returns through the pulmonary veins to the left atrium, and flows from the left atrium through the mitral valve, into the left ventricle. The left ventricle, in turn, pumps the blood through the body. As the heart beats, the atria contract to pump the blood into the ventricles, and then the ventricles contract, during a phase of the heart rhythm referred to as "systole," to pump the blood through the lungs and through the body.

For proper pumping action, the mitral valve must close when the left ventricle contracts. In a disease state known as mitral valve insufficiency, the mitral valve does not close properly, and a significant portion of the blood in the left ventricle is pumped back from the ventricle into the left atrium when the left ventricle contracts. This diminishes the pumping efficiency of the heart. Mitral valve insufficiency is a relatively common condition and afflicts about 4 million people in the United States alone, with about 250,000 new diagnoses of this condition every year. About 50,000 procedures are done every year to alleviate mitral valve insufficiency.

One surgical approach involves implantation of a porcine valve or a mechanical valve in place of the mitral valve. This procedure requires open heart surgery with long recuperation time, and exposes the patient to high risk of complications. Many of the individuals who need mitral valve repair are elderly, which tends to aggravate the difficulties associated with open heart surgery.

Another common surgical approach to repairing mitral valve insufficiency is annuloplasty. In this approach, a wire is wrapped around the mitral annulus, a ring of collagenous tissue surrounding the opening of the mitral valve, to contract the annulus. This improves the performance of the mitral valve. The mitral valve has two major leaves. If the opening of the valve is contracted, as by annuloplasty, the leaves are positioned closer to one another and form a better seal during systole. Annuloplasty as commonly practiced requires a major thoracic surgery with substantial recuperation time and risk of complications.

As disclosed, for example, in U.S. Pat. Nos. 6,306,133; 6,355,030; 6,485,489; 6,669,687; and 7,229,469, it has been proposed to insert a catheter-like device bearing a transducer such as an electrode or ultrasonic transducer into the heart and actuate the transducer so as to heat the mitral annulus, denature the collagen fibers which constitute the annulus, and thereby shrink the annulus. In theory, such a procedure could bring about shrinkage of the annulus and repair mitral insufficiency in much the same manner as traditional annuloplasty. However, all of these proposals have involved positioning of one or more transducers in contact with the mitral annulus during the procedure. It is difficult to provide such accurate positioning of a transducer within a beating heart. Although it is possible to momentarily halt the heartbeat, perform the procedure and then restart the heart, this adds considerable risk to the procedure. Moreover, localized heating of the annulus by a transducer in contact with the annulus introduces the further risk of damage to the epithelial cells overlying the annulus with attendant risk of thrombus formation after surgery.

Perhaps for these reasons, none of these proposals has been widely adopted. Accordingly, prior to the present invention, there has remained a need for a useful and reliable procedure for mitral valve repair.

II. SUMMARY OF THE INVENTION

One aspect of the present invention provides methods of treating a cardiac valve such as the mitral valve of a human or other mammalian subject. Methods according to this aspect of the present invention desirably include the step of positioning an emitter unit which incorporates an ultrasonic transducer in proximity to the valve without completely occluding the annulus of the valve. The positioning step desirably is performed so that the ultrasonic transducer is spaced apart from the annulus itself. For example, the emitter unit desirably includes an expansible structure such as a balloon, and the ultrasonic transducer is disposed within the expansible structure so that the when the structure is expanded to an operative condition, at least a portion of the structure is spaced apart from the ultrasonic transducer. Thus, when the structure is positioned in engagement with the mitral annulus, the transducer is spaced apart from the mitral annulus. Desirably, the transducer is also cooled by circulating fluid in the balloon to prevent any thrombus formation caused by heating of the transducer during operation.

As further discussed below, the expansible structure may be brought into engagement with the left posterior aspect of the mitral annulus so that the ultrasonic transducer is disposed within the annulus, closer to the posterior aspect than to the anterior aspect of the mitral annulus, and closer to the right aspect of the mitral annulus than to the left aspect, but nonetheless spaced apart from the posterior and left aspects. The transducer may be actuated so as to emit ultrasonic waves. The ultrasonic waves tend to heat the posterior and left aspects of the mitral annulus preferentially. As further discussed below, heating of the posterior aspect is particularly desirable, in that the posterior aspect is rich in collagen and tends to shrink readily with heating.

Preferably, the expansible structure in its expanded condition does not completely occlude the opening of the mitral valve. For example, where the expansible structure incorporates a balloon, the balloon desirably has a maximum diameter smaller than the diameter of the mitral annulus. The step of advancing the emitter unit may include advancing an elongated catheter having the emitter unit mounted thereon into a chamber of the heart, and positioning the catheter so as to position the expansible structure within the annulus of the valve. Where the valve to be treated is the mitral annulus, the catheter desirably is advanced into the left atrium through the right atrium, and through an opening formed in the inter-atrial septum. The step of advancing the catheter may include advancing a delivery sheath into the chamber of the heart and steering a distal region of the sheath, and advancing the catheter through the sheath. For example, the delivery sheath may be advanced into the left atrium, whereupon a distal portion of the sheath is steered in a downward direction, toward the mitral annulus.

The method preferably further includes the step of placing a guidewire extending through the catheter so that the guidewire extends from the left atrium through the mitral valve and into the left ventricle, and the positioning step includes positioning the catheter on the guidewire so that the portion of the catheter bearing the emitter unit is at least partially positioned within the mitral annulus by the guidewire.

As further discussed below, the steerable sheath desirably in combination with the guidewire provides a relatively simple and reliable way of positioning the emitter unit, which allows the emitter unit to remain in place in the beating heart long enough to perform the procedure.

Methods of treating mitral valve insufficiency according to a further aspect of the invention desirably include the step of preferentially applying energy to a selected portion of the mitral annulus, which portion is remote from the aortic valve, so as to heat and contract collagen in that portion of the annulus and thereby shrink the mitral annulus. Methods according to this aspect of the invention may include steps similar to those discussed above, and preferably include applying energy to the mitral annulus by positioning a transducer spaced from the selected portion of the annulus, but closer to the selected portion of the annulus than to other portions of the annulus, and actuating the transducer. Most preferably, the transducer is an ultrasonic transducer.

Yet another aspect of the invention provides apparatus for treating a cardiac valve of a mammalian subject. Apparatus according to this aspect of the invention desirably includes an elongated catheter having proximal and distal regions and an emitter unit including an ultrasonic transducer and an expansible structure carried on the distal region of the catheter. Most preferably, the expansible structure is constructed and arranged to hold the transducer spaced apart from an annulus of the valve when the expansible structure is in an operative, expanded condition, and the emitter unit is disposed in proximity to the valve. The expansible structure most preferably is constructed and arranged so that the expansible unit will not completely occlude the annulus of the valve. The expansible structure also may be arranged to preferentially position the transducer within the mitral valve annulus so that the left posterior aspect of the annulus lies within the near field region of the transducer.

Apparatus according to this aspect of the invention most desirably further includes a delivery sheath having proximal and distal ends, and a sheath steering structure carried on the sheath and operative to selectively bend a region of the sheath. The catheter and the emitter unit desirably are constructed and arranged so that the distal region of the catheter and the emitter unit can be advanced into a chamber of the heart through the sheath. The catheter may also include a catheter steering mechanism carried on the catheter and operative to selectively bend a bend region of the catheter proximal to the emitter unit. The apparatus may also include a guidewire, the catheter being constructed and arranged so that the catheter can be advanced over the guidewire, the guidewire can be advanced through the catheter, or both.

Most preferably, the expansible element includes a balloon, and the balloon has a major diameter smaller than the major diameter of the annulus of the valve to be treated. For example, where the apparatus is intended to treat the mitral valve of a human subject, the balloon desirably has a major diameter of about 30 mm or less. Desirably, the balloon has a proximal portion and a distal portion extending distal to the proximal portion. The distal portion of the balloon desirably has a smaller cross-sectional area than the proximal portion of the balloon when the balloon is in an inflated condition. As further discussed below, the transition between the proximal and distal portions of the balloon may be used to mechanically engage the mitral annulus so as to further stabilize the position of the balloon and transducer during the procedure.

In alternative embodiments the expansible structure comprises two or more individually extendable wires that may to selectively deployed to permit the balloon to be stabilized at a preferred position within the mitral valve annulus.

Further objects, features, and advantages of the present invention will be more readily apparent from the detailed described of the preferred embodiments set forth below, taken in conjunction with the accompanying drawings.

III. BRIEF DESCRIPTION OF THE DRAWINGS

FIG. 1 is a diagrammatic view of a component used in apparatus according to one embodiment of the invention.

FIG. 2 is a fragmentary diagrammatic view of the component shown in FIG. 1 in a different operating condition.

FIG. 3 is a diagrammatic view depicting a further component of the apparatus according to the embodiment of FIGS. 1 and 2.

IV. DETAILED DESCRIPTION OF THE INVENTION

Figure 4:
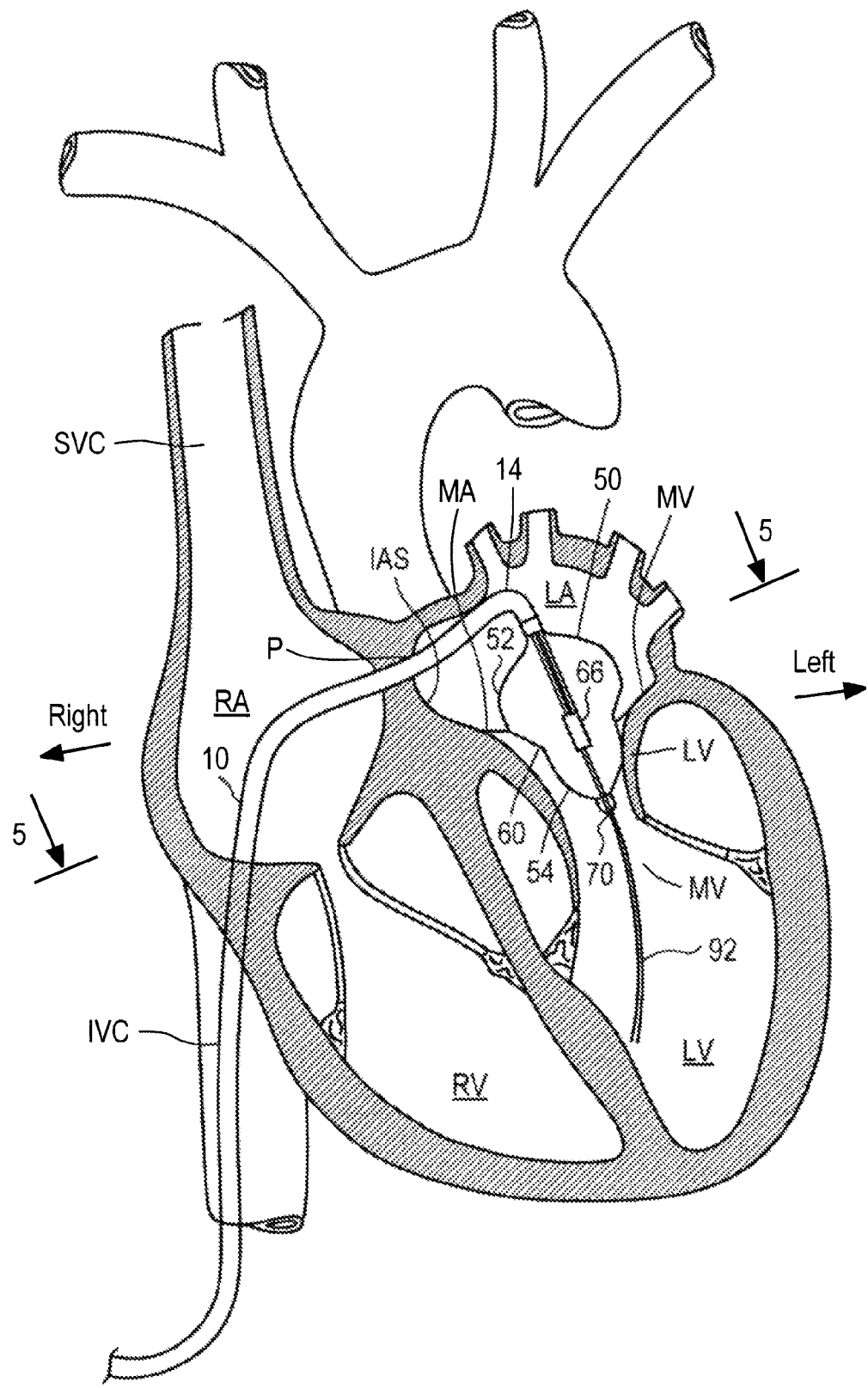
FIG. 4 is a diagrammatic coronal sectional view of a human heart with the apparatus of FIGS. 1-3 in an operative condition.

Referring to FIGS. 1-3, apparatus according to one embodiment of the invention includes sheath 10 and energy-emitting catheter 30.

Sheath 10 generally is in the form of an elongated tube having proximal end 12, distal end 14 and proximal-to-distal axis 13. As used in this disclosure with reference to elongated elements for insertion into the body, the term "distal" refers to the end which is inserted into the body first, i.e., the leading end during advancement of the element into the body, whereas the term "proximal" refers to the opposite end. Sheath 10 has interior bore 15 extending between its proximal and distal ends. Desirably, sheath 10 includes relatively stiff wall section 16 extending from its proximal end to juncture 18, and relatively limber distal wall section 20 extending from juncture 18 to distal end 14. Pull wire 22 is slidably mounted in proximal wall structure 16 and connected to distal wall section 20. Pull wire 22 is linked to pull wire control device 24, which can be manipulated by a physician during use of the apparatus. By actuating the pull wire control, the physician can pull on wire 22 and bend the distal region of the sheath in a predetermined direction transverse to the proximal-to-distal direction, as depicted schematically in FIG. 2. The structure of sheath 10 and pull wire control 24 may be generally as shown in U.S. Published Patent Application No. 2006-0270976 ("the '976 Publication"), the disclosure of which is incorporated by reference herein. As discussed in greater detail in the '976 Publication, transition 18 desirably is oblique to the proximal-to-distal axis 13 of the sheath, with stiff section 16 extending to distal-most point 25 on a first side of the sheath, and the pull wire desirably is arranged to bend the sheath only in the direction toward the first side.

Sheath 10 desirably also is arranged so that at least the proximal section is "torquable." That is, at least the proximal section of the sheath is arranged to transmit torsional motion about axis 13 from proximal end 12 along the axial extent of the sheath. Thus, by turning the proximal end of the sheath, the distal end of the sheath can be rotated about proximal-to-distal axis 13. As best appreciated with reference to FIG. 2, when the sheath is in the curved or bent configuration achieved by tension on the pull wire, rotational motion of the distal end will swing the bent section around proximal-to-distal axis 13. Thus, by combined pulling on the pull wire and rotational motion, distal end 14 of the sheath can be aimed in essentially any desired direction. As disclosed in the aforementioned '976 Publication, the pull wire control can be incorporated into a handle which is physically attached to proximal end 12 of the sheath. Thus, the physician can maneuver the sheath by actuating the pull wire control and turning the handle, desirably with one hand, during the procedure.

Referring now to FIG. 3, the inventive apparatus further includes elongated catheter 30 configured to be inserted through interior bore 15 of sheath 10. Catheter 30 has proximal end 32, distal end 34 and proximal-to-distal axis 33. Catheter 32 desirably incorporates principal bore 36 extending from its proximal end to its distal end. The catheter, like sheath 10 discussed above, may incorporate relatively stiff proximal wall portion 38 and relatively limber distal portion 40, with transition 42 between the proximal and distal wall sections. The catheter may be equipped with pull wire 44 which is linked to pull wire control 46. These structural features may be similar to those discussed above with reference to the sheath. Here again, the pull wire control may be actuated to bend the catheter in directions transverse to proximal-to-distal axis 33 of the catheter. The catheter also may be torquable about its axis, so that the distal end of the catheter can be bent in directions transverse to proximal-to-distal axis 33 of the catheter, and rotated around the axis as discussed above in connection with sheath 10.

An expansible structure, illustratively in the form of balloon 50 is mounted to distal end 34 of catheter 30. In the inflated, operative condition depicted, the balloon is generally in the form of a surface of revolution about a central axis coincident with proximal-to-distal axis 33 of the catheter. Balloon 50 has proximal section 52 with diameter $d_p$ of about 20 mm, and distal section 54 which has a maximum diameter $d_d$ at juncture 56 between distal section 54 and proximal section 52. Distal section 54 tapers inwardly from this diameter to tip 58 at the distal end of the balloon. The balloon has a relatively abrupt change in diameter over relatively short transition 60 between the proximal section and the distal section. Desirably, the balloon is formed from a polymer such as nylon and has a wall thickness of about 8 microns to about 30 microns. The dimensions of the balloon are given in the inflated condition shown in FIG. 3. When deflated, the balloon desirably collapse inwardly to form a relatively small diameter structure. The balloon may be fabricated by blow-molding using techniques that are known in the art.

A tubular, cylindrical ultrasonic transducer 66 is mounted inside balloon 50. Transducer 66 desirably is coaxial or nearly coaxial with the balloon, and is arranged so that the transducer extends axially over at least part of the transition region 60 of the balloon. The axial center point of the transducer may be disposed at an axial location near the juncture between proximal portion 52 and distal portion 54 of the balloon, so that part of the axial length of the transducer is disposed within proximal potion 52 and part of the axial length of the transducer is disposed within distal portion 54. Merely by way of example, transducer 66 may have an axial length of about 6 mm and an outside diameter of about 2-3 mm. The proximal end of the transducer may be in transition region 60 or in proximal region 52 of the balloon. Transducer 66 is carried on tubular metallic support 68 extending from distal end 34 of catheter 30 to tip 58 of the balloon. Support 68 defines an interior bore (not shown) which communicates with main bore 36 of catheter 30. The tubular support 68 extends to distal tip 58 of the balloon so that the interior of tubular support 68 communicates with the exterior of the balloon through port 70 at the distal tip of the balloon. Transducer 66 is mounted on the support so that interior wall 72 of the tubular transducer is spaced apart from exterior wall of support 68. The space between the interior of the transducer and the exterior of the support communicates with the interior space within balloon 50. As disclosed, for example, in U.S. Published Patent Application No. 20060270975, the disclosure of which is incorporated by reference herein, support 68 may include telescopic elements which move axially with respect to one another to accommodate inflation and deflation of the balloon. Transducer 66 desirably is formed from a ceramic piezoelectric material. The tubular transducer has metallic coatings (not shown) on its interior and exterior surfaces. These metallic coatings are connected to a ground wire and a signal wire (not shown) which extend through wiring support tube 74 to the distal end of the catheter. These wires extend through catheter 30 to the proximal end of the catheter, and are configured to be connected to ultrasonic excitation source 76. Metallic support tube 68 and transducer 66 desirably are configured so that the interior surface of the tubular transducer is spaced apart from the exterior surface of tube 68 by a gap distance which corresponds to approximately one-half the wavelength of the ultrasonic energy to be applied, i.e., about 83 microns for 9 MHz ultrasonic energy propagating in water. As further discussed below, this promotes efficient operation of the transducer, with ultrasonic energy reflected at the exterior surface of support tube 66 reinforcing ultrasonic energy propagating within the transducer, so as to provide ultrasonic energy directed outwardly from external surface 66 of the transducer.

The interior space within balloon 50 is connected to circulation device 80 for circulating a liquid, preferably an aqueous liquid, through the balloon. Device 80 includes inflow pump 82 and outflow pump 84. The inflow pump is connected to inflow passage 86 extending through catheter 30 to the balloon, whereas outflow pump 84 is connected to separate outflow passage 88 extending through the catheter to the balloon. Pumps 82 and 84 are connected to coolant circuit 90 for supplying a liquid coolant, desirably an aqueous liquid such as saline solution. The coolant circuit 90 may include elements such as a tank for holding the circulating coolant, a refrigerating coil, or the like for providing a supply of liquid at a controlled temperature, desirably at or below body temperature. The circulation device also includes a control circuit (not shown) for controlling the flow into and out of the balloon. Merely by way of example, the control elements may include motor control devices linked to drive motors associated with pumps 84 and 82 for controlling the speed of operation of the pumps. Such motor control devices can be used, for example, where the pumps are positive displacement pumps such as peristaltic pumps. Alternatively or additionally, the control elements may include structures such as controllable valves connected in the fluid circuit for varying resistance of the circuit to fluid flow. A pressure sensor (not shown) optionally may be mounted in the balloon and electrically connected to the control circuitry. As further discussed below, during operation, circulation device 80 continually circulates the aqueous fluid through the balloon and maintains the balloon under a desired pressure, most preferably about 3 pounds per square inch (20 Kpa).

Figure 5:
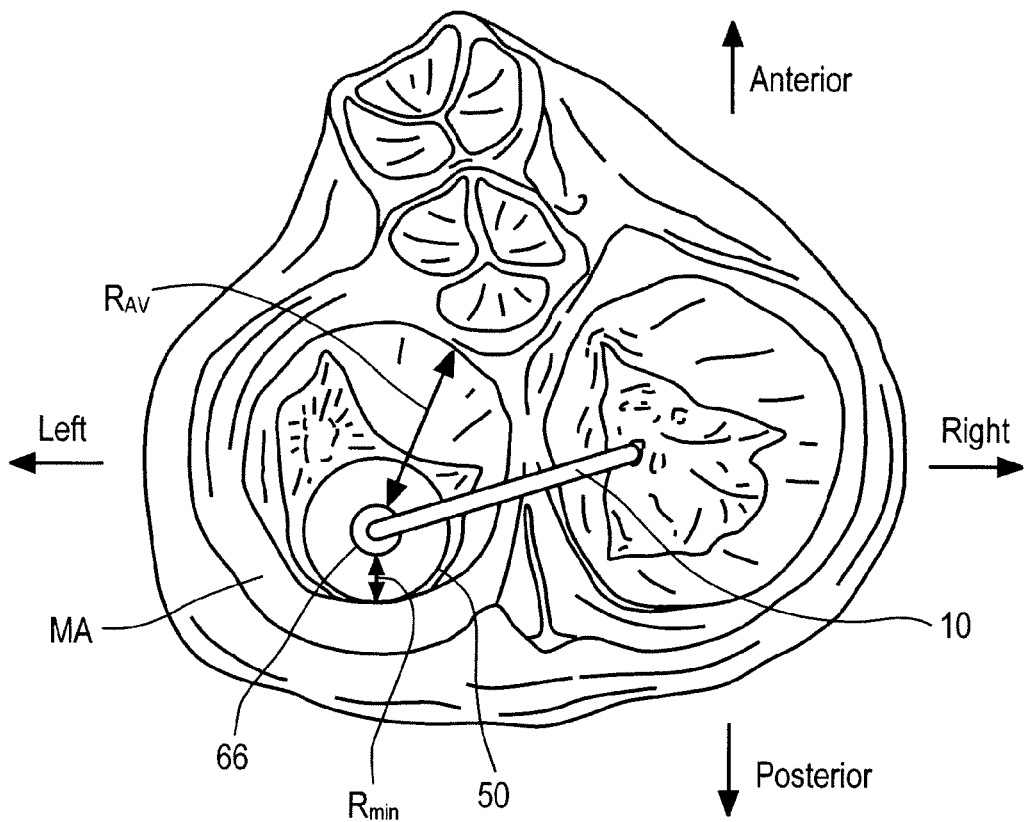
FIG. 5 is a diagrammatic axial sectional view of the heart along line 5-5 in FIG. 4, also in conjunction with the apparatus of FIGS. 1-3, but with the atria of the heart removed for clarity of illustration.

Referring now to FIGS. 4 and 5, in a method according to one embodiment of the invention, a conventional device such as a Brockenbaugh needle is advanced through the venous system as, for example, through the inferior vena cava and into the right atrium. The needle is used to form a puncture P (FIG. 4) through the inter-atrial septum IAS dividing the right atrium RA from the left atrium LA. After the puncture the needle is withdrawn and sheath 10 is advanced over a dilator. Guidewire 92 may be advanced into the left atrium, and optionally through the mitral valve MV into the left ventricle.

Sheath 10 then is advanced over guidewire 92 until distal end 14 of the sheath extends into the left atrium through puncture P. During this step, the dilator (not shown) may be disposed within bore 14 of sheath 10, so that the dilator surrounds the guidewire and the sheath surrounds the dilator. Once the sheath has been advanced into the left atrium, the dilator may be removed. With balloon 50 in a deflated condition, catheter 30 is advanced over guidewire 92 and through bore 14 of sheath 10. During this advancement, the guidewire extends through port 70 and through support tube 68 and main bore 36 of the catheter. Catheter 30 is advanced until distal end 34 of the catheter and balloon 50 project out from the distal end of sheath 10. Once balloon 50 is disposed within the left atrium, circulation apparatus 80 (shown in FIG. 1) is actuated to inflate the balloon to the desired pressure, desirably about 3 psi (20 Kpa).

Sheath 10 is steered so as to aim the distal end of the sheath downwardly toward the mitral valve MV and rearwardly, toward the posterior surface of the heart and the posterior aspect of the mitral valve ring, also referred to as the annulus fibrosus. This is accomplished by bending the distal end of the sheath using pull wire 22 and pull wire control as discussed above with reference to FIGS. 1 and 2. If catheter 30 is equipped with a pull wire, as discussed above with reference to FIG. 3, the distal tip of the catheter also may be bent and turned so as to aim it posteriorly. Because the sheath extends into the left atrium from the right atrium, the balloon tends to lodge against the left side of the mitral valve ring. The steering operations may also be used to promote disposition of the balloon towards the left side of the mitral valve ring.

Guidewire 92 is positioned such that the guidewire extends through the mitral valve and into the left ventricle. The guidewire may extend further and curve back into the aorta through the aortic valve. The combined effects of the guidewire, the steerable sheath, and, if employed, the steerable catheter all tend to position balloon 50 generally in the location illustrated in FIG. 4, with the balloon extending through the mitral annulus MA of the mitral valve MV, with distal region 54 of the balloon disposed between the leaflets LV of the mitral valve.

Balloon 50 is configured so that juncture 56 tends to engage the mitral annulus. This engagement is facilitated by transition 60 between distal portion 54 and proximal portion 52 of the balloon, and is further facilitated by maintaining a moderate pressure within the balloon, which permits balloon 50 to be indented to some degree by the mitral annulus. This physical engagement between the balloon and the mitral annulus helps to maintain the balloon in the desired operative position relative to the heart. Also, engagement of the balloon is reliably maintained by continued biasing of the balloon into engagement with the mitral annulus by the sheath and catheter, and by the guidewire. Thus, the balloon can be retained in the operative position shown while the heart continues to beat.

With the balloon in the operative position, ultrasonic transducer 66 is aligned with the mitral annulus, but spaced therefrom. That is, radial lines directed outwardly from the outer surface of transducer 66, in a plane perpendicular to the axis of the tubular transducer, would intercept the mitral annulus.

The desired position of the lumen and transducer is further illustrated in FIG. 5, where the heart is seen in an axial view from the top, with the atria and associated structures removed for ease of illustration. Note that balloon 50 is lodged against the mitral annulus, closer to the left side of the mitral annulus than to the right side, and closer to the posterior aspect of the mitral annulus than to the anterior aspect. Transducer 66 is held spaced apart from the mitral annulus, but is disposed closer to the posterior and left aspects of the mitral annulus than to the anterior and front aspects. For example, the radial distance $R_{MIN}$ from the surface of transducer 66 to the left posterior aspect of the mitral annulus may be on the order of 1 cm. The corresponding distances from the surface of transducer 66 to other locations around the mitral annulus are greater. For example, the distance RAV from the surface of transducer 66 to the aortic valve may be on the order of 2 cm or more.

Preferably, balloon 50 does not completely occlude the mitral annulus, and thus does not completely occlude blood flow from the left atrium into the left ventricle. Moreover, the maximum diameter of the balloon is less than the maximum diameter of the mitral annulus, such that leaflets LV of the mitral valve provide reasonable sealing of the mitral valve against backflow from the left ventricle into the left atrium during systole. The leaflets may bear on the balloon and on one another during systole. The smooth surfaces of the balloon minimize damage to the leaflets. Because the heart remains functional while the balloon is in its operative position, the balloon may be retained in this operative condition for a sufficient length of time, for example, several minutes, to perform the procedure. The physician can verify proper placement of the balloon using fluoroscopic or other imaging techniques. To enhance such fluoroscopic techniques, the liquid circulated through the balloon may include a radiological non-ionic contrast agent. Alternatively, placement of the balloon can be visualized by transesophageal echocardiographic imaging, also known as TEE imaging, or other echocardiographic technique. When an echocardiographic technique is utilized, balloon 50 may be initially filled with a fluid containing an ultrasonic contrast medium to allow for easy visualization. The balloon is manipulated as necessary under visualization and thereby positioned in the heart. If an ultrasonic contrast medium is employed, it should be purged from within the first balloon and replaced by a liquid which does not attenuate or reflect ultrasound before actuation of the ultrasonic transducer.

With the balloon and transducer in the operative position, ultrasonic excitation source 76 (FIG. 1) actuates transducer 66 to emit ultrasonic waves. Merely by way of example, the ultrasonic waves may have a frequency of about 1 MHz to a few tens of MHz, most typically about 9 MHz. The transducer typically is driven to emit, for example, about 10 watts to about 100 watts of acoustic power, most typically about 30 to about 40 watts. The actuation is continued for about 20 seconds to about a minute or more, most typically about 40 seconds to about 90 seconds. Optionally, the actuation may be repeated several times as, for example, about 5 times. The frequencies, power levels, and actuation times may be varied from those given above.

The ultrasonic waves generated by the transducer propagate generally radially outwardly from the transducer, outwardly through the liquid within the balloon to the wall of the balloon and into the surrounding blood and tissue. The ultrasonic waves impinge on the tissues of the heart surrounding the balloon, and particularly on the mitral annulus. Propagation of the ultrasonic waves is essentially independent of contact between the balloon and the solid tissues of the heart, such as the mitral annulus. Because all of the tissues, the liquid within the balloon and the blood surrounding the balloon have approximately the same acoustic impedance, there is little or no reflection of ultrasonic waves at interfaces between the liquid within the balloon and the blood outside the balloon; at interfaces between the blood and the tissue; or at the interface between the saline within the balloon and the solid tissue in areas where the balloon does contact the mitral annulus.

Essentially all of the mitral annulus lies within the "near field" region of the transducer. Within this region, the outwardly spreading cylindrical beam of ultrasonic waves tends to remain collimated and has an axial length (the dimension of the beam perpendicular to the plane of the drawing in FIG. 5) approximately equal to the axial length of the transducer. For a cylindrical transducer, the extent of the near field region is defined by the expression $L^2/\lambda$, where L is the axial length of the transducer and $\lambda$ is the wavelength of the ultrasonic waves. At distances from the transducer surface greater than $L^2/\lambda$, the beam begins to spread axially to a substantial extent. However, for distances less than $L^2/\lambda$, the beam does not spread axially to any substantial extent. Therefore, within the near field region, at distances less than $L^2/\lambda$, the intensity of the ultrasonic waves decreases linearly, in proportion to distance from the transducer surface, as the beam spreads radially. Thus, the posterior and left regions of the mitral annulus receive substantially more intense ultrasonic waves than the anterior and right regions. This is advantageous, inasmuch as the posterior and left regions contain particularly high concentrations of collagen fibers. The ultrasonic energy directed into these regions is particularly effective in shrinking the mitral annulus. Moreover, the moderate levels of ultrasonic energy directed towards the front and right aspects of the mitral annulus are unlikely to damage sensitive structures such as the aortic valve disposed in proximity to the front and right aspects of the mitral annulus.

The ultrasonic energy applied by the transducer is effective to heat and thus denature collagen fibers within the mitral annulus, thereby shrinking the annulus. It is believed that the shrinkage occurs principally in the left and posterior aspects of the mitral annulus. Because the transducer is spaced apart from the mitral annulus, the ultrasonic energy is applied over the entire mitral annulus simultaneously. There is no need for extreme precision in positioning of the balloon and transducer relative to the heart. Thus, the procedure is relatively simple and reliable. The mitral annulus tends to shrink to some extent immediately upon application of the ultrasonic energy; some additional shrinkage may occur during the weeks following treatment. Shrinkage of the mitral annulus tends to improve the sealing action of the leaflets and reduce or cure mitral valve insufficiency.

Because the ultrasonic energy is dissipated and converted to heat principally inside the mitral annulus, rather than at its surface, the procedure does not damage the surface of the heart which is in contact with the blood, and hence does not provoke thrombus formation. Circulation of the cooled liquid through the balloon during the procedure helps to cool the transducer and essentially prevents direct heat transfer between the transducer and the epithelial lying at the surface of the mitral annulus where the lining contacts the balloon. Those regions of the epithelium which are not in contact with the balloon are cooled by blood flowing over them during the procedure with continued operation of the heart.

Because the procedure can be performed rapidly, the balloons need not be maintained in position for a prolonged time. Additionally, because the procedure does not require intimate contact between the balloon and the mitral annulus or other heart structures, the procedure, including application of the ultrasonic energy, can be performed while the heart continues to beat. Further, balloon 50 is designed to minimize the amount of energy that may be misdirected away from the mitral annulus, to the mitral leaflets or other tissues not targeted by the therapy.

After completion of the ultrasonic application procedure, the balloon is deflated, and the apparatus is withdrawn from the subject's body.

EXAMPLE 1

Figure 6:
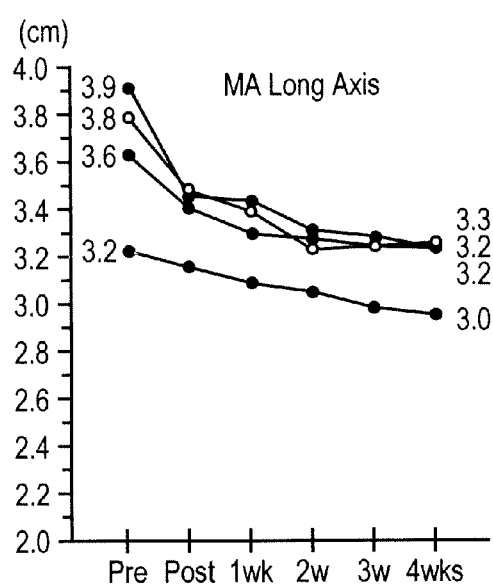
FIGS. 6 and 7 are graphs depicting results achieved in certain experiments.
Figure 7:
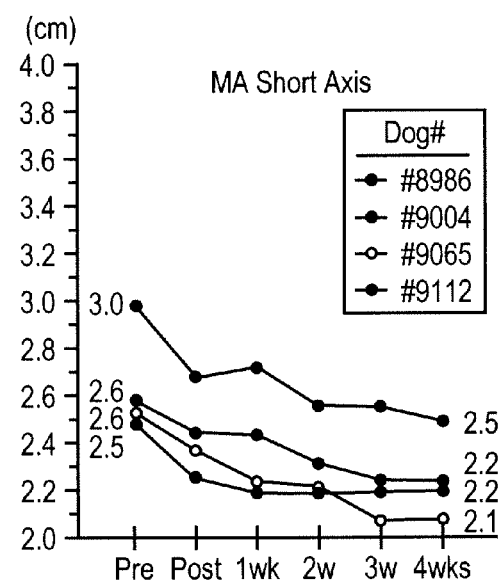

Four dogs are treated using apparatus and techniques substantially as described above with reference to FIGS. 1-5. The dimensions of the mitral annulus are measured in vivo by imaging techniques pretreatment, immediately post-treatment and at one, two, three, and four weeks post-treatment. The results are as indicated in FIGS. 6 and 7, and demonstrate substantial shrinkage of the mitral annulus. The dogs did not evidence adverse effects from the procedure. Their circulation and cardiac rhythm remained intact after the procedure. Upon dissection, the heart did not exhibit scarring of the epithelial lining.

Figure 8:
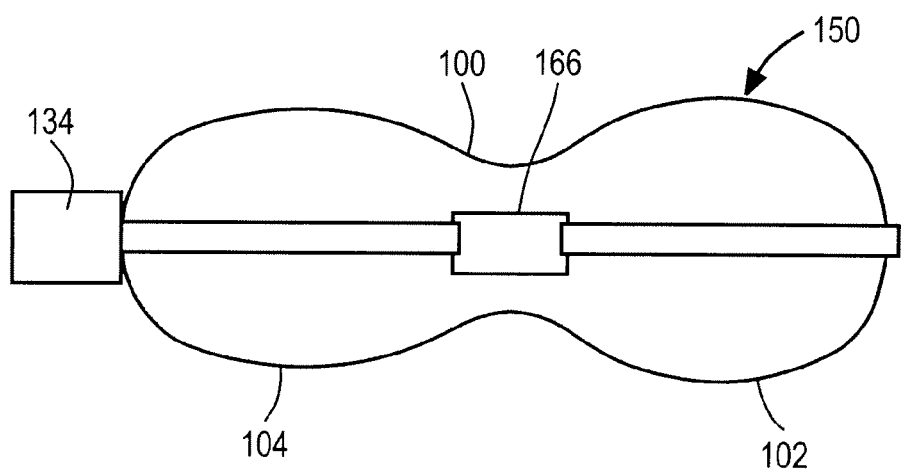
FIG. 8 is a fragmentary diagrammatic sectional view of apparatus according to a further embodiment of the invention.

Referring now to FIG. 8, apparatus according to a further embodiment of the invention is described, and incorporates balloon 150 and transducer 166 mounted on distal end 134 of a catheter. In this embodiment, however, balloon 150, in the inflated condition as depicted, has narrow section 100 surrounding transducer 166 and distal region 102 distal to the narrow section, the distal section being of slightly larger diameter than narrow section 100. The balloon also has proximal section 104 proximal to the narrow section. In this embodiment as well, the shape of the balloon facilitates engagement of the balloon with the mitral annulus and stable positioning of the apparatus during use.

Figure 9A:
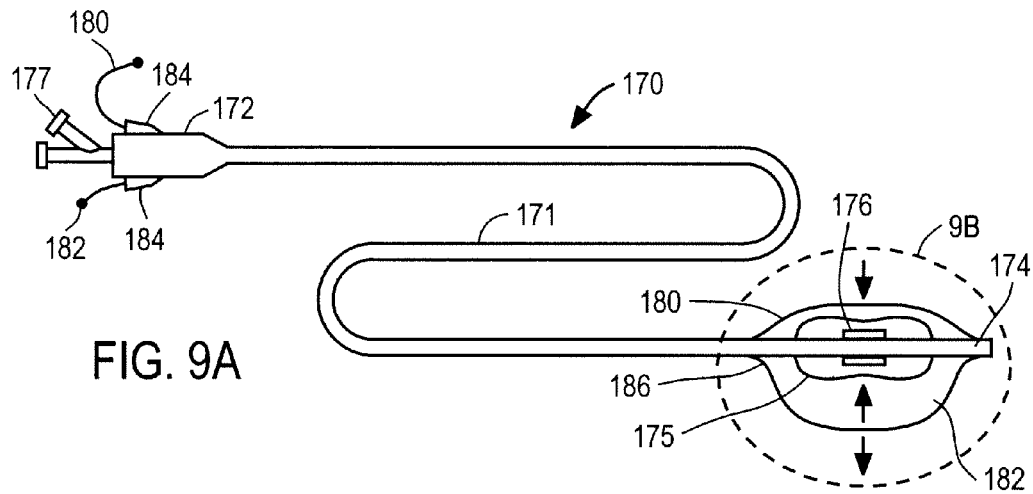
FIGS. 9A and 9B, are respectively, a plan view depicting apparatus according to an alternative embodiment of the invention and a detailed view of the distal end of the apparatus.
Figure 9B:
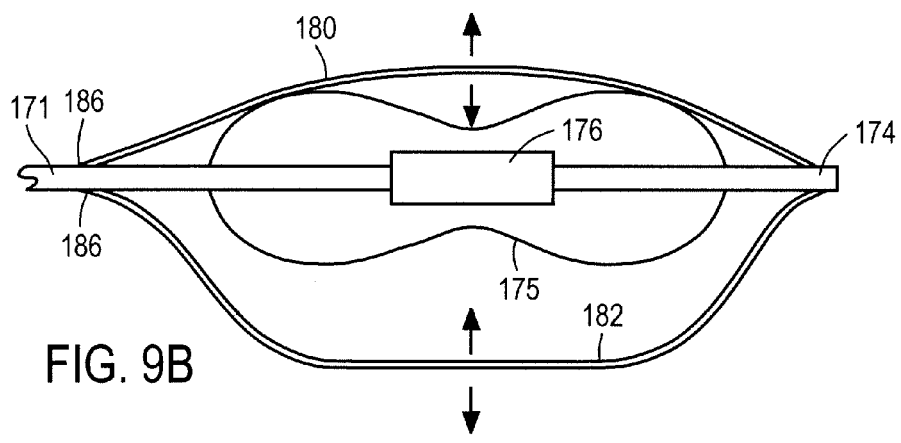
Figure 10:
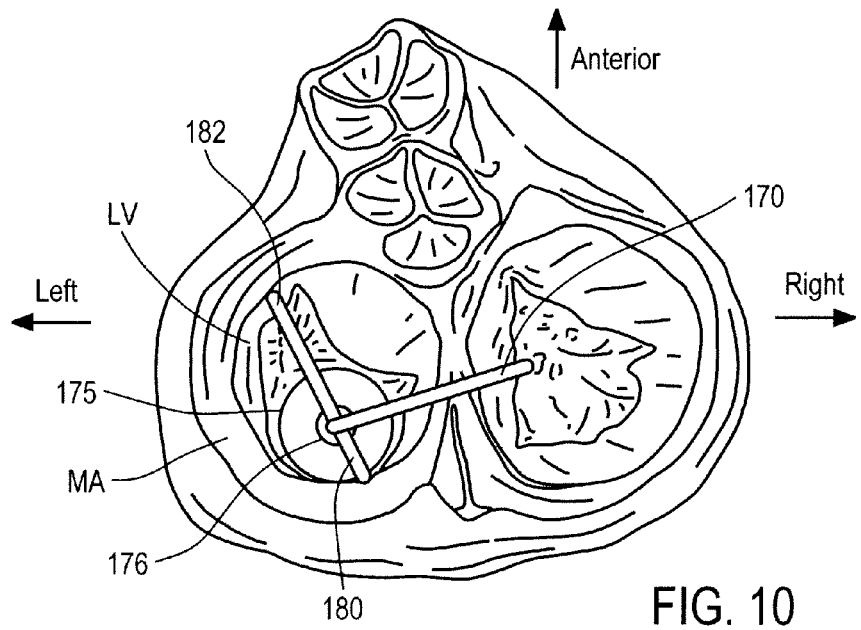
FIG. 10 is a diagrammatic axial sectional view of the heart similar to that of FIG. 5, showing positioning of the apparatus of FIG. 9 within the mitral valve, again with the atria of the heart removed for clarity of illustration.

Referring now to FIGS. 9A, 9B and 10, a further alternative embodiment of the inventive apparatus is described, including catheter 170, which may be used with or without sheath 10 described above. Catheter 170 includes elongated shaft 171, which may be steerable as described above, having proximal end 172 and distal end 174. Balloon 175, which illustratively is a double-lobed balloon as depicted in FIG. 8, is disposed adjacent distal end 174, and surrounds ultrasonic transducer 176. Balloon 175 is coupled via inflation port 177 to circulation circuit 90 (FIG. 1) which inflates and circulates coolant through the balloon. As for preceding embodiments, balloon 175 is inserted in a deflated state and then inflated with an aqueous liquid, such as saline solution, which surrounds transducer 176 and conducts ultrasonic energy from transducer 176 to the mitral annulus. Ultrasonic transducer is similar in construction to that described with respect to the embodiment of FIG. 3, and emits ultrasonic energy in a substantially radial direction in the near field region, as described above.

Catheter 170 further includes individually movable struts 180 and 182 that extend from proximal end 172 to distal end 174 through interior lumens (not shown) of the catheter body. Struts 180 and 182 exit the lumens via outlets 184 at proximal end 172, and may include compression rings, thumb screws or other suitable means to lock the struts at a selected position. The distal ends of struts 180 and 182 exit through skives 186 in the exterior wall of catheter 170 at a location proximal of balloon 175, pass around the outside of balloon 175, and are fastened to distal end 174 of catheter 170. Struts 180 and 182 preferably comprise a strong, resilient and flexible plastic material, or a metal or metal alloy wires, such as a superelastic nickel-titanium alloy, and may have a circular, oval or rectangular cross-section. While two struts 180 and 180 are depicted in FIG. 9, it is to be understood that a greater or lesser number of struts may be employed in catheter 170.

Referring to FIG. 9B, struts 180 and 182 are slidably disposed in the lumens of catheter 170 and configured to be independently moved from a delivery state, in which the struts are collapsed against deflated balloon 175, to a deployed state, in which each of struts 180 and 182 is extended by advancing it in a distal direction through its respective outlet 184 and skive 186. In this manner, the distal region of each strut 180 and 182 selectively may be caused to bow outward in the deployed state (as indicated by arrows in FIG. 9B). By individually adjusting the extent to which the distal regions of struts 180 and 182 bow outward, the clinician can adjust the positioning of balloon 175, and thus transducer 176, relative to the surrounding tissue. As illustratively depicted in FIG. 9B, strut 182 may be extended to a much greater extent than strut 180, thereby causing balloon 175 and transducer 176 to be positioned closer to strut 180 than to strut 182.

As further illustrated in FIG. 10, when catheter 170 is deployed in the mitral valve, struts 180 and 182 when expanded will extend to the commissures of the mitral valve leaflets. Struts 180 and 182 then may be individually adjusted to position balloon 175 and transducer 176 at the location preferred by the methods of the present invention, e.g., so that the left posterior aspect of the mitral annulus is in the near field region of transducer 176, as described for the embodiment of FIGS. 1-5. Because struts 180 and 182 preferably are formed from a strong, resilient and flexible material, they are capable of accommodating motion of the beating heart while retaining the balloon and transducer at a selected location for the duration of the treatment. Once the mitral annulus has been reduced a selected amount via deposition of ultrasonic energy, as determined, for example, using fluoroscopic imaging, balloon 175 may be deflated. Struts 180 and 182 then may be collapsed to the delivery state, and catheter 170 may be removed.

In the embodiment of FIGS. 9 and 10, balloon 175 illustratively includes the dual-lobed shape depicted in FIG. 8, and when inflated the narrowed region of the balloon assists in longitudinally positioning the transducer relative to mitral annulus MA. In further alternative embodiments, balloon 175 may include a larger proximal region and narrower distal region, like balloon 50 of the embodiment of FIG. 1, or may include a balloon of uniform diameter along its length. Balloon 175 further may include a proximal-facing or distal-facing reflector element, as described for additional embodiments herein below. Preferably, however, balloon 175 does not fully occlude the mitral valve when deployed, and thus permits uninterrupted flow of blood through the left side of the heart during the procedure.

Figure 11:
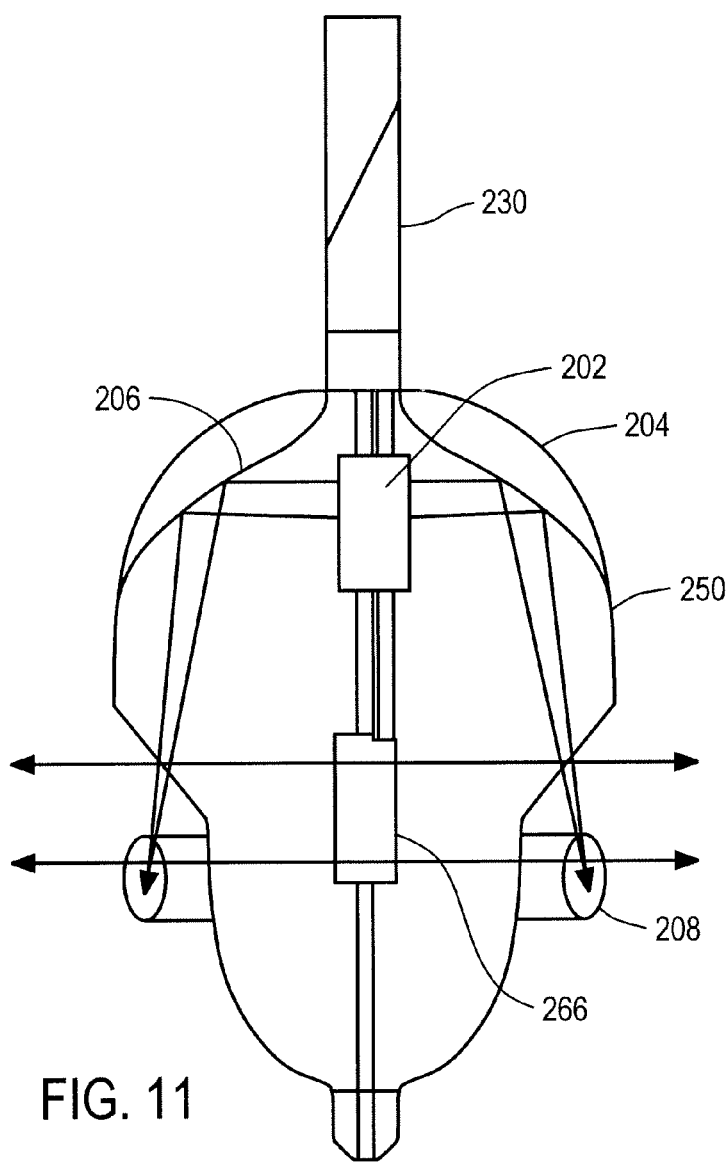
FIG. 11 is a diagrammatic sectional view depicting apparatus according to yet a further embodiment of the invention.

Referring now to FIG. 11, apparatus according to yet another embodiment of the invention includes catheter 230 having balloon 250 and first transducer 266 similar to the corresponding features of the embodiments discussed above with reference to FIGS. 1-5. Catheter 230 further includes second transducer 202 mounted proximally to transducer 266. Second balloon 204 surrounds a portion of the proximal region of balloon 250 aligned with second transducer 202. A separate lumen (not shown) is provided in catheter 230 for inflation and deflation of second balloon 204.

In operation, second balloon 204 is inflated with a gas such as carbon dioxide. Balloon 250 in its inflated condition is configured to have parabolic surface 206 in the regions surrounding transducer 202. As described, for example, in U.S. Pat. No. 6,635,054 and U.S. Published Patent Application No. 2004-0176757, the disclosures of which are hereby incorporated by reference, the interface between the liquid inside first balloon 250 and the gas inside second balloon 204 forms a reflector for ultrasound. The ultrasonic energy emitted from second transducer 202 is reflected at this interface and directed substantially into annular focal region 208, forward of transducer 202 and outside of balloon 250.

As described in the patent and publication mentioned in the preceding paragraph, the forwardly directed ultrasound energy may be used to form a substantially ring-like lesion in cardiac tissue. For example, the balloon may be positioned so that focal region 208 lies within the cardiac tissue surrounding a pulmonary vein, and transducer 202 may be actuated to direct ultrasonic energy into this focal region, thereby ablating the cardiac tissue around the pulmonary vein, e.g., to treat atrial fibrillation. First transducer 266 can be used in the manner discussed above to treat mitral insufficiency. The ultrasonic energy from first transducer 266 propagates radially outwardly in the manner described above, and does not encounter the reflective interface formed by the gas in second balloon 204.

Catheter 230, which may be configured to be steerable similarly to sheath 10, may be used alone or in conjunction with a steerable sheath, like sheath 10 described above, to reposition the apparatus from the position required for treatment of atrial fibrillation to the position required for treatment of mitral insufficiency, or the reverse. The capability of treating both atrial fibrillation and mitral insufficiency with a single catheter-based device provides a significant advantage, inasmuch as a significant proportion of patients who suffer from atrial fibrillation also suffer from mitral insufficiency, and vice-versa. Gas-filled second balloon 204 can be readily visualized in echocardiographic techniques, as it is highly reflective to ultrasound.

In a variant of this embodiment, first and second transducers 202 and 266 may be replaced by a single transducer which can be moved by the operator between the positions indicated for transducers 202 and 266. In a further variant, the emitter structure may include only a single transducer at the location indicated for second transducer 202. In this variant, the emitter structure is arranged to emit ultrasound only in the forward or distal direction, into ring-like focal region 208. For treatment of mitral valve insufficiency, the balloon may be positioned in the atrium, with the distal end of the balloon extending through the mitral annulus so that focal region 208 is aligned with the mitral annulus.

In a further variant, the balloon may be reversed, so that second balloon 204 is positioned within the ventricle, between the leaflets of the mitral valve. In this arrangement, the ultrasonic energy is emitted in the retrograde direction, toward the atrium. In this configuration, gas-filled second balloon 204 blocks transmission of ultrasonic energy to the leaflets, and thus prevents damage to the leaflets. Thus, the possibility of misdirecting energy into the mitral leaflets and the left ventricle is largely eliminated.

Figure 12:
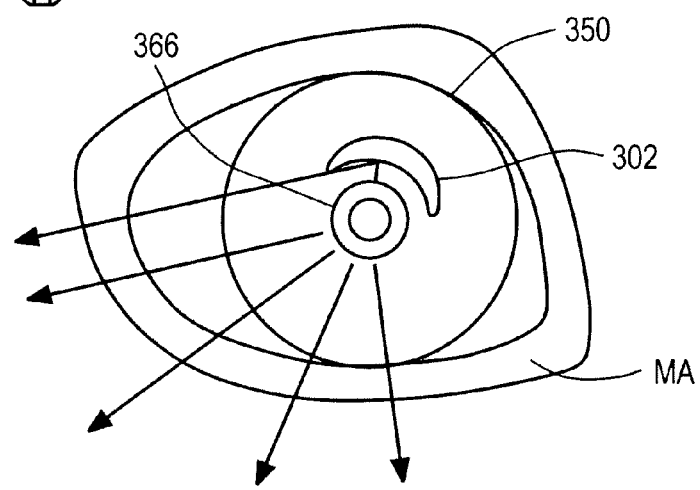
FIG. 12 is a diagrammatic sectional view depicting apparatus according to yet another embodiment of the invention.

Numerous other variations and combinations of the features discussed above can be utilized without departing from the present invention as defined by the claims. For example, expansible structures other than those described above may be used. For example, an expandable basket-like structure can be used in place of the balloon. In still other embodiments, the emitter structure can include reflective or blocking structures for selectively directing ultrasonic waves from the transducer over only a limited range of radial directions. For example, the apparatus of FIG. 12 includes reflective balloon 302 which may be filled with a gas, for selectively directing the ultrasonic waves from transducer 366 over only a limited range of radial directions. Here again, the ultrasound passes through balloon 350 to impinge on the surrounding mitral annulus.

In still other arrangements, the ultrasonic transducer itself may have a directional emission pattern. Another embodiment is to utilize a transducer designed to be activated by different frequencies at designed sectors of its circumference. By varying the wall thickness of the transducer, it will resonate at different frequencies thus allowing for the electronic control of emitted energy to create an optimal energy pattern that is asymmetric.

Alternatively, asymmetric energy delivery can be achieved using segmented transducers (example: individual arc-lengths less than 360 degrees when combined form a 360 degree tubular transducer). In still other embodiments, focusing devices, such as lenses and diffractive elements can be employed. An annular lens surrounding a cylindrical transducer as shown, for example in U.S. Published Patent Application No. 2002-0068885, the disclosure of which is hereby incorporated by reference herein, may be used to narrow the axial extent of the emitted ultrasonic waves.

The route by which the apparatus is introduced into the heart can be varied from that discussed above. However, the atrial approach offers a safety advantage over a retrograde approach through the aortic valve because the risk of entangling the catheter with the chordae tendinae is much higher in a retrograde approach to the mitral valve through the ventricle. Also, it is not essential to use a catheter to place the expansible device. The emitter structure, including the transducer and the balloon or other expansible device as described above can be mounted on a short and relatively inflexible handle, so that the emitter structure can be placed by a minimally invasive surgical technique.

The state of the mitral annulus can be monitored by ultrasound imaging during the treatment. During treatment, the collagenous tissue changes its physical properties, and thus its ultrasound reflectivity when heated. These changes in tissue ultrasound reflectivity can be observe using ultrasonic imaging to monitor the formation of the desired lesion in the mitral valve. Doppler ultrasound can be used to monitor the blood flow during the procedure. Ultrasonic transducers for these purposes can be carried on the same catheter which carries the emitter unit, or on separate catheters or probes.

Other imaging modalities which can detect heating can also be used to monitor the treatment. For example, magnetic resonance imaging can detect changes in temperature.

In a further variant, ultrasonic range detection can be used to monitor the size of the mitral annulus during treatment. For example, pinging devices can be mounted adjacent to transducer 66 (FIG. 3). One configuration is to use two-pair devices at diametrically opposite locations, on opposite sides of the central axis of the balloon. The purpose of the pinging devices is to monitor the acute progress (mitral annulus shrinkage) during the course of ablation. The ultrasound pinging devices measure relative distance to the surrounding tissue. By comparing the relative distance between the opposite walls (e.g., anterior-posterior) measured by pinging devices, the operator can monitor the resultant mitral annulus shrinkage to a preplanned size.

In yet another variant, the application of the ultrasonic energy can be gated to the cardiac cycle. The cardiac cycle can be monitored by conventional EKG techniques, by ultrasonic blood flow measurement, or by other techniques. Excitation unit 76 may be arranged, for example, to deliver the ultrasonic waves only at a preselected point in each cardiac cycle.

The apparatus and methods discussed above are particularly useful in treating mitral valve insufficiency, but also may be used to treat other valves in the circulatory system as, for example, the tricuspid valve of the heart.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. An apparatus for ablating cardiac tissue while reducing disruption of natural blood flow through a cardiac valve of a mammalian subject, the apparatus comprising:

an elongated catheter having proximal and distal regions; and an emitter unit including an ultrasonic transducer and an expandable balloon positioned along a distal portion of the elongated catheter, the expandable balloon comprising a proximal portion, a distal portion and a transition region therebetween, the transition region extending from a distal end of the proximal portion to a proximal end of the distal portion, wherein a diameter of the expandable balloon, when expanded, at the distal end of the proximal portion is larger than a diameter of the balloon at the proximal end of the distal portion, wherein the expandable balloon, when expanded, comprises an abrupt change in diameter along the transition region, the distal end of the proximal portion of the expandable balloon, when expanded, being angled relative to a proximal end of the transition region by an angle greater than zero degrees, wherein the distal portion of the expandable balloon, when expanded, tapers in the distal direction from the proximal end of the distal portion to a distal end of the distal portion, wherein the ultrasonic transducer extends axially at least partially over the transition region of the expandable balloon, wherein the expandable balloon surrounds the ultrasonic transducer, wherein the ultrasonic transducer is configured and arranged such that, in use, when ultrasonic energy is emitted, the emitted ultrasonic energy causes shrinkage of the annulus of the valve, wherein, in use, the expandable balloon is constructed and arranged to hold the transducer spaced apart from the annulus of the valve and to retain the leaflets of the valve out of a path of the ultrasonic energy when the expandable balloon is deployed in situ and expanded, and the ultrasonic transducer is generally aligned with the annulus of the valve; wherein the apparatus is configured so that, when the emitter unit is positioned within the valve, (i) the leaflets of the valve contact an exterior of the expandable balloon and form a seal against the expandable balloon, and (ii) an outer diameter of the expandable balloon is less than a cross-sectional dimension of the annulus of the valve so that the expandable balloon does not completely occlude the annulus thereby permitting blood to uninterruptedly flow through the valve, between the leaflets and the exterior of the expandable balloon, wherein the distal portion of the expandable balloon comprises a smooth outer surface so as to reduce the likelihood of damage to the leaflets of the valve.

2. The apparatus of claim 1 wherein the catheter is configured, when in use, to position the emitter unit adjacent to a posterior aspect of the annulus.

3. The apparatus of claim 1, wherein the distal portion of the expandable balloon includes a smaller cross-sectional area than the proximal portion of the expandable balloon when the expandable balloon is in an expanded condition during use.

4. The apparatus of claim 1, wherein the distal portion of the expandable balloon comprises a curved outer profile from the transition region to the distal end of the distal portion.

5. The apparatus of claim 1, wherein there is a decrease in diameter at the transition region between the proximal and distal portions to facilitate aligning the ultrasonic transducer with the annulus of the valve.

* * * * *